United States Patent [19]
Haber et al.

[11] Patent Number: 5,423,752
[45] Date of Patent: * Jun. 13, 1995

[54] VARIABLE PROPORTION DISPENSER WITH CARTRIDGE REPLACEMENT ASSEMBLY

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[ * ] Notice: The portion of the term of this patent subsequent to Dec. 21, 2010 has been disclaimed.

[21] Appl. No.: 924,620

[22] Filed: Jul. 31, 1992

[51] Int. Cl.$^6$ ............................................. A61M 37/00
[52] U.S. Cl. .................................. 604/86; 604/82; 604/191; 222/137; 222/309; 222/145.7
[58] Field of Search .............. 222/137, 145, 283, 309, 222/327, 386, 86; 604/82, 186, 191, 86

[56] References Cited

U.S. PATENT DOCUMENTS

| | | |
|---|---|---|
| 3,162,217 | 12/1964 | Poli, Jr. et al. . |
| 3,248,950 | 5/1966 | Pursell et al. . |
| 3,283,727 | 11/1966 | Rodrigues, Jr. . |
| 3,343,539 | 9/1967 | Moorhouse . |
| 3,831,602 | 8/1974 | Broadwin . |
| 4,040,420 | 8/1977 | Speer . |
| 4,044,757 | 8/1977 | McWhorter et al. . |
| 4,273,257 | 6/1981 | Smith et al. . |
| 4,381,778 | 5/1983 | Kozam et al. . |
| 4,610,666 | 9/1986 | Pizzino . |
| 4,631,055 | 12/1986 | Redl et al. . |
| 4,666,430 | 5/1987 | Brown et al. . |
| 4,801,434 | 1/1989 | Kido et al. . |
| 4,846,405 | 7/1989 | Zimmermann . |
| 4,874,368 | 10/1989 | Miller et al. . |
| 4,883,472 | 11/1989 | Michel . |
| 4,962,868 | 10/1990 | Borchard . |
| 4,978,336 | 12/1990 | Capozzi et al. . |
| 5,019,048 | 5/1991 | Margolin . |
| 5,199,949 | 4/1993 | Haber et al. ............... 604/191 |
| 5,240,146 | 8/1993 | Smedley et al. ........... 604/91 |
| 5,271,257 | 12/1993 | Haber et al. ............... 604/191 |
| 5,281,198 | 1/1994 | Haber et al. ............... 604/191 |

FOREIGN PATENT DOCUMENTS

| | | |
|---|---|---|
| 0313519 | 10/1988 | European Pat. Off. . |
| 313519 | 4/1989 | European Pat. Off. . |
| 984352 | 7/1951 | France . |
| 1051010 | 1/1954 | France . |
| 1054173 | 2/1954 | France . |
| 137660 | 10/1901 | Germany . |
| 245816 | 5/1987 | Germany . |
| 733168 | 7/1955 | United Kingdom . |

OTHER PUBLICATIONS

Brochure, "How to Use Your *NovolinPen198*," Sep. 1990, Novo Nordisk A/S.
Brochure, "Product Information for the *Novo Pen* Insulin Delivery System," issue 1988, Squibb-Novo, Inc.
Brochure, "Product Information for the *Novolin-Pen TM, Insulin Delivery System*, System," issue 1988, Squibb-Novo, Inc.

*Primary Examiner*—C. Fred Rosenbaum
*Assistant Examiner*—N. Kent Gring
*Attorney, Agent, or Firm*—Townsend & Townsend Khourie & Crew

[57] ABSTRACT

A variable proportion dispenser (2c) includes a housing (12c) which houses two pharmaceutical cartridges (6b). A reciprocating drive assembly includes drive stems (36c) extending from the pistons (46b) of each cartridge, a limit guide (76c) removably mounted to the housing, and a sliding body (66e, 300) mounted to the housing through the limit guide. Two one-way drivers (326) and threaded dosage adjusters (60c) are carried by the sliding body. Each one-way driver drives the drive stem into the cartridge through a drive surface to provide a range of dose selections. The user can thus control the amount and proportion of each pharmaceutical dispensed during each delivery stroke for each dispensing cycle. The housing is separable from the remainder of the dispenser, preferably using a cartridge release assembly (302), to allow spent cartridge to be replaced. Use of the cartridge release assembly also causes the one-way drivers to release the drive stems to permit the drive stems to be returned to their original positions.

27 Claims, 39 Drawing Sheets

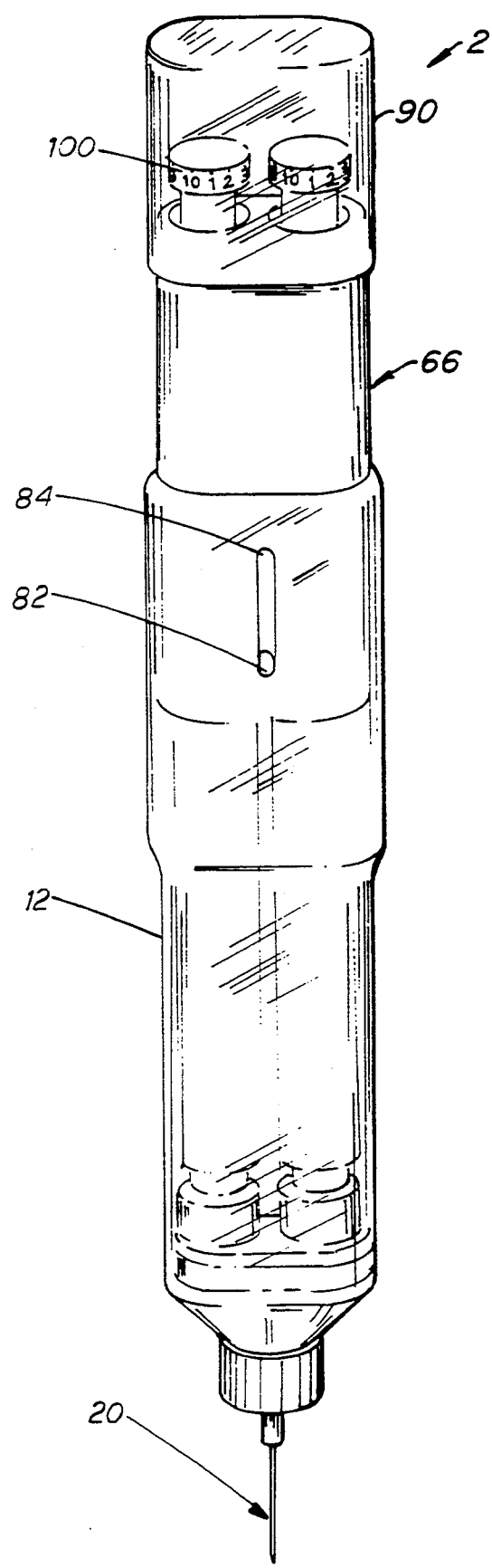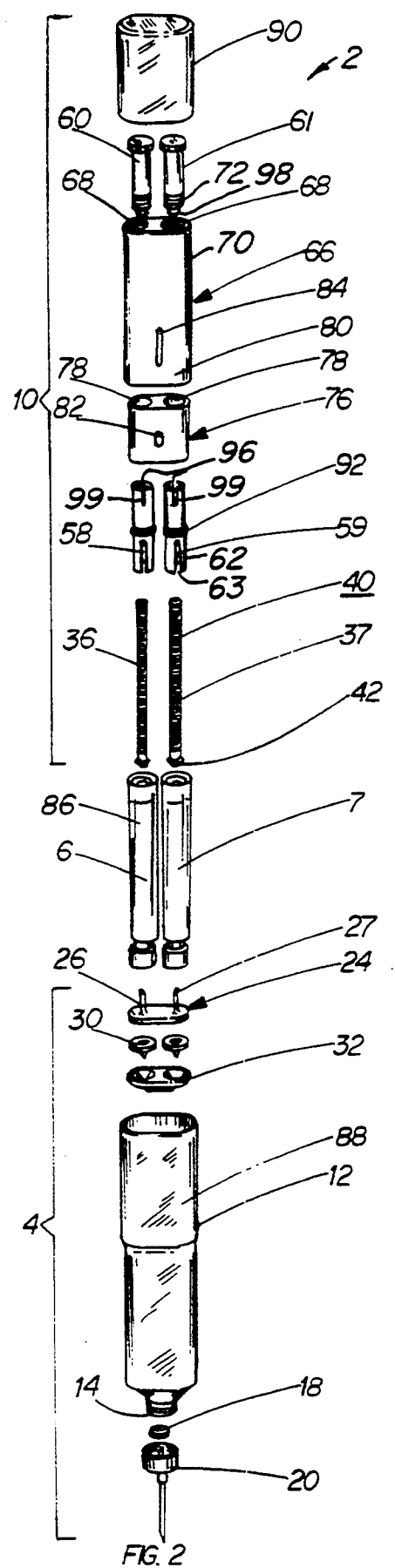
FIG. 1
FIG. 2

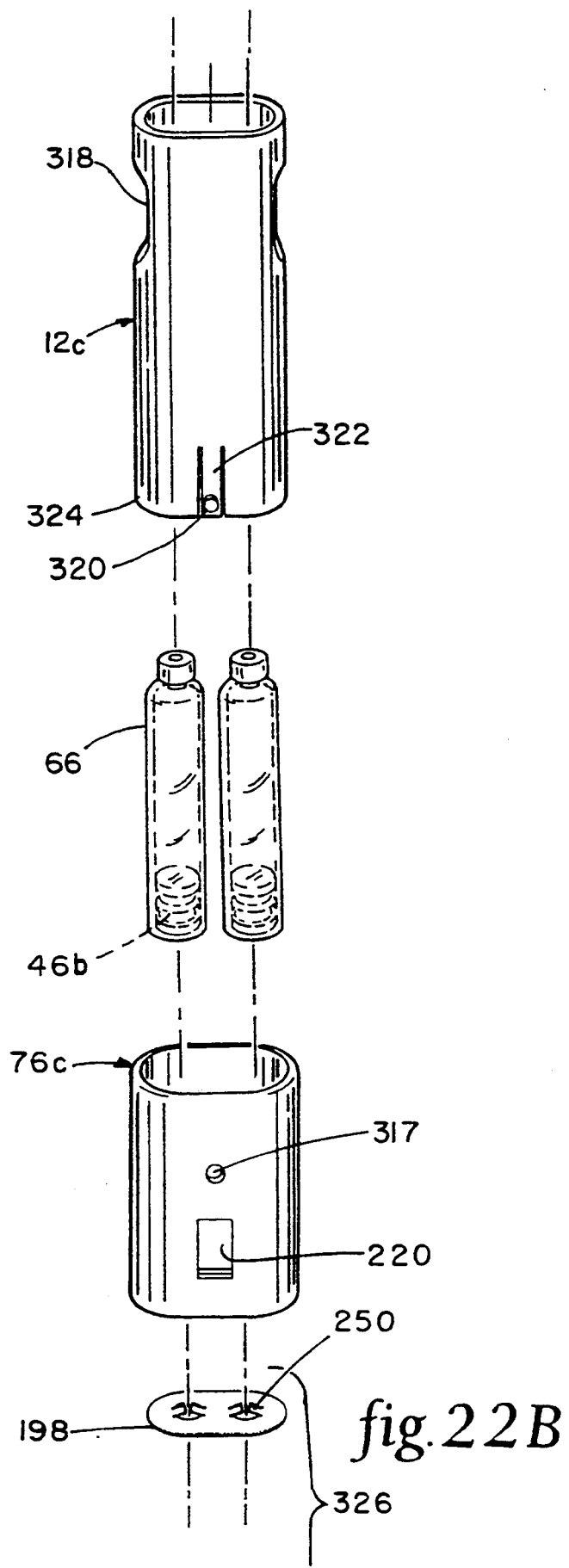

– –

VARIABLE PROPORTION DISPENSER WITH CARTRIDGE REPLACEMENT ASSEMBLY

CROSS REFERENCE TO RELATED APPLICATIONS

This is related to U.S. patent application Ser. No. 07/862,090 filed Apr. 2, 1992 entitled Variable Proportion Dispenser now U.S. Pat. No. 5,253,785. This application is also related to U.S. patent application Ser. No. 07/808,717 filed Dec. 17, 1991 entitled Variable Proportion Dispenser now U.S. Pat. No. 5,240,146, which is a continuation-in-part of U.S. Pat. application Ser. No. 07/628,271 (now abandoned) filed Dec. 14, 1990 entitled Variable Proportion Dispenser, and a continuation-in-part of U.S. patent application Ser. No. 07/718,398 filed Jun. 21, 1991, entitled Multiple Pharmaceutical Syringe now U.S. Pat. No. 5,199,949, which is a continuation-in-part of U.S. patent application Ser. Nos. 07/667,319 (now U.S. Pat. No. 5,147,323 issued 15 Sep. 1992) and 07/668,278 now U.S. Pat. No. 5,286,258, both filed Mar. 8, 1991 and entitled Multiple Cartridge Syringe and Multipharmaceutical Syringe, respectively, the disclosures of which are incorporated by reference.

BACKGROUND OF THE INVENTION

Frequently a physician will prescribe two or more medications to be taken by a patient either simultaneously or as close to simultaneously as practical. This is often the case in prescribing insulin. Two basic types of insulin are most frequently prescribed: regular, a fast-acting variety, and NPH, an intermediate-acting variety. Additionally, a longer-acting type of insulin called ultralente is also available. These types of insulin differ in their onset and duration of action. Regular insulin typically has the quickest onset and the briefest duration of action. The onset and duration of insulin may be modified by chemical manipulations which include precipitation with protamine or suspension with isophane or zinc. Injectable insulin is derived from pigs and cattle, and a semi-synthetic genetically-engineered human form is available commercially.

Regardless of the final chemical composition or origin of the insulin prescribed, the physician frequently advises the patient to mix two or more types of insulin and to inject them at least once a day. Some patients respond best to a schedule of two or three daily doses, usually in conjunction with meals. Frequently trial-and-error type of evaluation is practiced to arrive at the correct dosing and combination for the individual patient. However, after this initial adjustment period, the patient may be maintained on the same dose and proportion of insulins for many weeks or months assuming that the patient's diet, activity, and state of health remain reasonably constant or predictable. An example of a typical mixture and ratio of insulins is 70% NPH and 30% regular insulin injected just prior to a meal.

The implications of insulin therapy for the patient generally include the need for two separate sets of insulin injection syringes and needles. This is because the patient will usually draw a predetermined amount of insulin from each of two vials. A sophisticated patient may be able to use a single syringe and simply draw up the correct amount from each separate insulin vial. However, he may prefer to use two separate needles because of the danger of mixing two types of insulin by using a needle "contaminated" with one type of insulin and accidentally getting some of the first insulin into the second vial from which he draws the second insulin. If the patient is not sophisticated or not adept at drawing up insulin from a vial into a syringe, he would need two needles and two syringes. He may find that he has drawn up too much insulin and then he wishes to return the excess to the vial. If he is using a single syringe, he cannot return the excess to the vial if he is presently attempting to draw insulin from the second vial. The problem is compounded if the patient is on a regimen requiring three types of insulin. The problem of getting the correct amount and proportion of each type of insulin prescribed is an everyday difficulty which the diabetic patient may face two or three times a day.

Besides insulin, other medications may be advantageously prescribed as a simultaneous or near-simultaneous dose. For example, pain medications of the opiate family are frequently prescribed together with antiemetics. The antiemetic drugs are often useful as potentiators of narcotic painkillers and additionally they may ameliorate some of the side effects of narcotics such as nausea and vomiting. For example, a patient who has chronic pain, such as that associated with metastatic cancer, may take 50 milligrams of meperidine (a narcotic) and 25 milligrams of hydroxyzine (an antiemetic) intramuscularly several times a day. Patients having chronic pain are often managed in a long-term care facility such as a nursing home. Alternatively, an outpatient setting is sometimes feasible if the patient or his family can administer medications.

Unfortunately, many patients requiring either chronic pain medication or insulin find that they have some difficulty with their eyesight. This may be especially true of the older age group. Additionally, diabetics who require insulin replacement frequently suffer deterioration of vision as a consequence of the diabetic process. Thus, people who are often in greatest need of multiple injected medications of a defined dose and proportion may ironically find their drug regimen most difficult to regulate precisely. Another problem arises in the context of long-term care facilities such as nursing homes. Frequently the nurse who administers injectable drugs is pressed for time on medication rounds. The time pressure is compounded if the care facility is constrained by budgetary or other non-medical concerns. A device which permits accurate dosing and proportion of two or more medications and which allows for repetitive dosing in the same proportions could be useful to a variety of patients in a variety of circumstances.

SUMMARY OF THE INVENTION

The present invention is directed to a variable proportion dispenser, especially useful for dispensing different types of insulin in amounts and proportions selected by the user. Once the combined dosage is selected, both in amount and proportion, the same dosage will be automatically provided for each actuation cycle of the dispenser. The invention, as an insulin delivery system, permits the total amount of the insulin injected and the proportion NPH and regular human insulin to be user selected.

The variable proportion dispenser includes a housing which houses two or more variable volume containers, typically pharmaceutical cartridges. A reciprocating drive assembly is used to dispense predetermined amounts of the contents of the cartridges in predetermined proportions. The amounts and proportions, once set, remain the same for each actuation of the drive assembly. The reciprocating drive assembly includes a sliding body mounted to the housing. The sliding body moves between first and second axial positions during each cycle of the dispenser.

The drive assembly also includes a one-way drive device carried by the sliding body and a drive stem engaged by the one-way drive device during each delivery stroke. The one-way drive device preferably includes a threaded dosage adjuster which mounts within a threaded hole within the sliding body. The one-way drive device also includes a reciprocating driver positioned between the dosage adjuster and the cartridge. The dosage adjuster and reciprocating driver are axially aligned and configured so that when the sliding body, and dosage adjuster therewith, are driven during the delivery stroke from the first position towards the second position, that is towards the cartridge, the opposed ends of the dosage adjuster and reciprocating driver engage and the reciprocating driver is driven towards the cartridge. The reciprocating driver has a lower end which engages the drive stem during the delivery stroke to drive the drive stem against the piston in the cartridge. The lower end of the reciprocating driver and the drive stem are configured so the reciprocating drive ratchets back over the drive stem during the return stroke. Thus, the reciprocating driver acts as a one-way linear driver.

The reciprocating driver, in this embodiment, preferably has a collar positioned to engage a driver stop associated with the housing to limit the movement of the reciprocating driver on the return stroke away from the cartridge. Whether or not the collar contacts the driver stop is determined by the axial position of the dosage adjuster within the sliding body. For example, if the dosage adjuster is fully threaded into the sliding body, the collar will typically not contact the driver stop so that the adjacent ends of the dosage adjuster and reciprocating driver remain engaged throughout the cycle. However, if the dosage adjuster is moved away from the fully threaded position a sufficient amount, then the collar will contact the driver stop before the sliding body has reached its first position on the return stroke. This causes the opposed ends of the dosage adjuster and reciprocating driver to disengage. During the next delivery stroke, during which the sliding body is moved from the first position to the second position, the dosage adjuster does not contact the reciprocating driver for an initial portion of the stroke. This results in a decrease in the volume of the contents driven from the cartridge. Also, by individually adjusting the dosage adjusters, the point at which the dosage adjusters contact their respective reciprocating drivers can be changed. This permits the user to adjust the proportions and amounts of the components dispensed from the cartridges during each delivery stroke.

Another aspect of the invention is the provision of a visual indicator which permits the user to easily determine the amount of each component which is to be delivered before the delivery stroke. In one embodiment this is achieved using a visual dose indicator which moves axially according to the proposed dose. A separate dose indicator is used for each component.

Some users may suffer from a certain degree of confusion; the simultaneous visual display of two (or more) dose indicators when setting the dose for each component could create problems for these users. With a two-component dispenser, it is preferred that the dose indicator for each component be visually perceptible from opposite sides of the dispenser. Thus, when a user sets the dose, by rotating the dose adjustor, only one dose indicator is visible. This helps to ensure that the user does not become confused as to the dose selected.

In the present embodiments the axial position of the reciprocating driver prior to the delivery stroke determines the dose. The visual indication of this axial movement can be magnified by the dose indicator. For example, assume that an axial movement of three millimeters by the reciprocating driver corresponds to one unit of medication. With the present invention, the dose indicator can be driven in such a way that the dose indicator moves six millimeters for every three millimeters the reciprocating driver moves. This permits the units of medication markings, typically carried by the sliding body, to be spaced twice as far apart as would otherwise be possible thus greatly enhancing ease of use and accuracy. Of course, other ratios between the movement of the dose indicator and the movement of the reciprocating driver, and thus of the piston within the cartridge (either greater than one-to-one or less than one-to-one) could be used as well.

In one embodiment the amplification is achieved by providing two sets of threads on the threaded dose adjustor. For example, a right-hand set of threads can be used to drive the dose adjustor within the sliding body and a left-hand set of threads, also on the dose adjustor, can be used to drive the dose indicator. The right-hand threads on the dose adjustor, which engage right-hand threads within the sliding body, cause the dose adjustor to move one pitch length for each rotation of the dose adjustor. However, the dose indicator engages the left-hand threads of the dose adjustor and is prevented from rotating with the dose adjustor but is allowed to move axially. This causes the dose indicator to move one pitch length along the left-hand threads of the dose adjustor. The threads for the indicator are preferably coextensive with the right-hand threads but have a much longer pitch length, such as three times the length. In such a case, the dose indicator will move within the sliding body four unit lengths for each unit length the dose adjustor moves within the sliding body.

After the delivery stroke, once the user returns the sliding body back to its predelivery stroke, the dose adjustor and the dose indicator will return to the same positions within the sliding body as before the delivery stroke. Thus, if the user wishes to repeat a stroke with the same proportions, no adjustments need to be made.

One of the primary advantages of the invention is that it permits the user to adjust both the quantity and proportion of the two components to be delivered by the dispenser. The setting stays the same for multiple doses without the need for any additional adjustment.

In a further embodiment the housing, and cartridges therewith, can be separated from the remainder of the dispenser. This permits the removal and replacement of spent cartridges. In addition, to permit re-use, the drive stems can be released from the one-way drivers to permit the drive stems to be returned to their initial positions.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall isometric view of a variable proportion dispenser made according to the invention with the sliding body in the first, pre-delivery position;

FIG. 2 is an exploded isometric view of the dispenser of FIG. 1;

DESCRIPTION OF THE PREFERRED EMBODIMENTS

FIG. 1 illustrates a variable proportion dispenser 2 particularly suited for dispensing insulin. As shown in FIG. 2, dispenser 2 includes broadly a housing assembly 4, first and second insulin containing cartridges 6, 7 and a reciprocating drive assembly 10.

Figure 3:
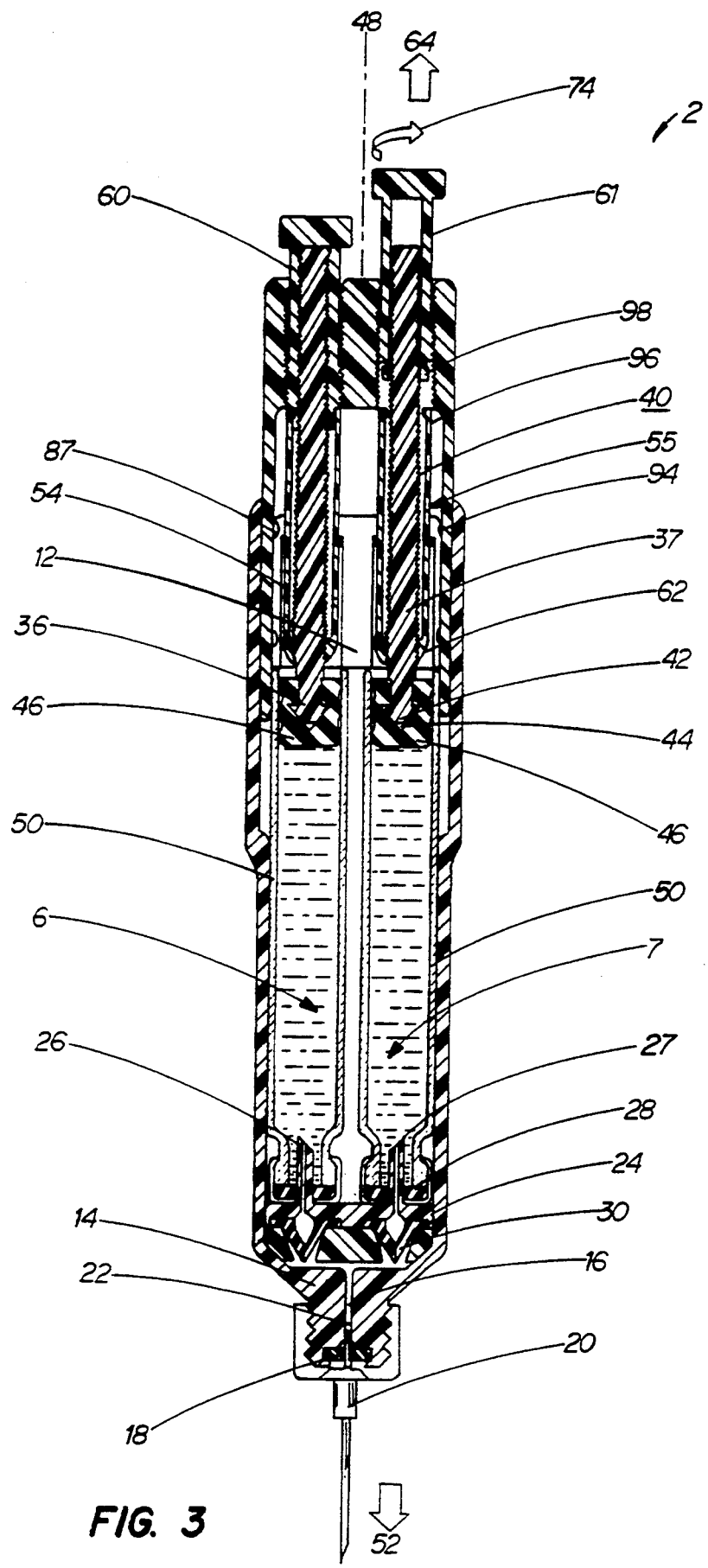
FIG. 3 is a cross-sectional view of the dispenser of FIG. 1 with the cap removed, the sliding body in the first, predelivery position and one of the dosage adjusters repositioned within the sliding body.

Turning now also to FIG. 3, housing assembly 4 is seen to include a housing 12, preferably made of a clear plastic material such as polycarbonate, so the user can see the contents of cartridges 6, 7. Housing 12 includes a threaded tip 14 having a central bore 16 formed therein. An elastomeric septum 18 is mounted to the end of tip 14. A double-ended needle assembly 20 has an inner end 22 which pierces septum 18 and is positioned within bore 16 to provide a conduit from bore 16 through needle assembly 20 during use. Needle assembly 20 is preferably replaced after each use.

Cartridges 6, 7 are housed within the interior of housing 12. A dual spike 24 having sharpened spike tips 26, 27 is used to pierce the septums 28 at the ends of cartridges 6, 7. A pair of elastomeric check valves 30 are positioned adjacent dual spike 24 by a check valve adapter 32. As shown in FIG. 3, this provides a pathway from the interiors of cartridges 6, 7, through spike tips 26, 27, past check valves 30, into bore 16 and through needle assembly 20. However, the capillary restrictions created within spike tips 26, 27 and needle assembly 20 and the restrictions provided by check valves 30 and septum 18 keep the contents of cartridges 6, 7 from leaking from dispenser 2.

Reciprocating drive assembly 10 includes first and second drive stems 36, 37 having serrated outer surfaces 40 and coned tips 42. Coned tips 42 are housed within complementary regions 44 formed within pistons 46 of cartridges 6, 7. Thus, movement of drive stems 36, 37 parallel to axis 48 will drive pistons 46 within the barrels 50 of cartridges 6, 7. Drive stems 36, 37 are driven in the direction of arrow 52 by one-way drive devices 54, 55. Drive devices 54, 55 include reciprocating drivers 58, 59 and dosage adjusters 60, 61. Devices 54, 55 are hollow to accommodate drive stems 36, 37. Drivers 58, 59 each include a stem engaging end 62 having serrations or teeth which complementarily engage the serrated outer surface 40 of its associated drive stem 36, 37. The serrations or teeth are configured such that movement of reciprocating drivers 58, 59 in the direction of arrow 52 causes stem engaging ends 62 to firmly grip the associated drive stems 36, 37, thus forcing piston 46 in the direction of arrow 52. However, movement in the direction of arrow 64, that is in the direction of the return stroke, allows stem engaging end 62, which has slits 63 which allow end 62 to dilate, to slide over serrated outer surface 40 so that the reciprocal movement of reciprocating drivers 58, 59 act in a ratcheting manner driving pistons 46 in the direction of arrow 52 but not in the reverse direction of arrow 64.

Reciprocating drive assembly 10 also includes a sliding body 66 having a pair of internally threaded holes 68 formed at one end 70 of sliding body 66. Dosage adjusters 60, 61 each include external threads 72 which engage threaded holes 68 to permit the user to adjust the axial positions of dosage adjusters 60, 61 relative to sliding body 66 as suggested in FIG. 3 by arrow 74.

Reciprocating drive assembly 10 also includes a limit guide 76 having parallel bores 78 through which reciprocating drivers 58, 59 and drive stems 36, 37 pass. The lower end 80 of sliding body 66 is hollow for receipt of limit guide 76. Limit guide 76 has an outwardly projecting rib 82, see FIGS. 1 and 2, which rides within an axially extending slot 84 formed in end 80 of sliding body 66. Limit guide 76 is secured to housing 12 through the attachment of rib 82 to the inner wall of housing 12. The upper portion 88 of housing 12 is enlarged to accommodate sliding body 66. Movement of sliding body 66 and dosage adjusters 60, 61 is limited by engagement of rib 82 with the ends of slot 84. Sliding body 66 includes projections 87 which engage appropriately positioned indentations 89, 91 formed in limit guide 76 to act as detents to help keep sliding body 66 in the pre-delivery and post-delivery positions.

Figure 3A:
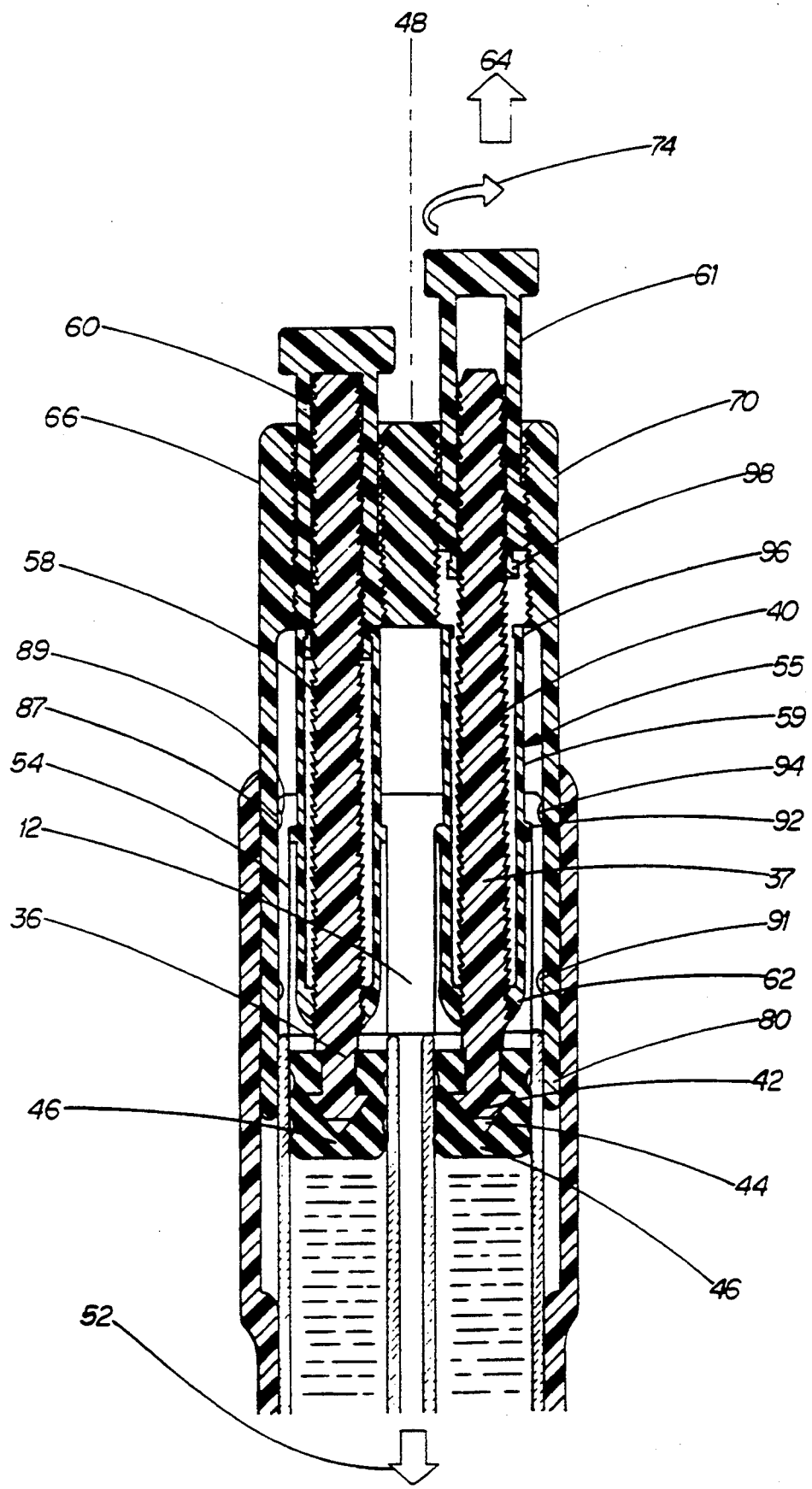
FIG. 3A is an enlarged view of a portion of the dispenser of FIG. 3.

Dispenser 2 is shown in FIG. 3 after a cap 90 has been removed, after sliding body has been moved from its second, post-delivery position of FIG. 1 to its first, predelivery position, and after dosage adjuster 61 has been adjusted by rotating in the direction of arrow 74. Doing so causes dosage adjuster 61 to separate from reciprocating driver 59 as shown in FIG. 3. This occurs because reciprocating driver has a collar 92 which engages an inwardly extending, annular driver stop 94 to prevent any further movement of reciprocating driver 59 in the direction of arrow 64. As seen in FIG. 3A, the ends 96, 98 of reciprocating driver 59 and the dosage adjuster 61 are configured to provide non-slip driving engagement when dosage adjuster 61 is moved in the direction of arrow 52 but for releasable engagement when dosage adjuster 61 is moved in the direction of arrow 64 once a sufficient separating force is applied between the reciprocating driver 59 and dosage adjuster 61.

Figure 4:
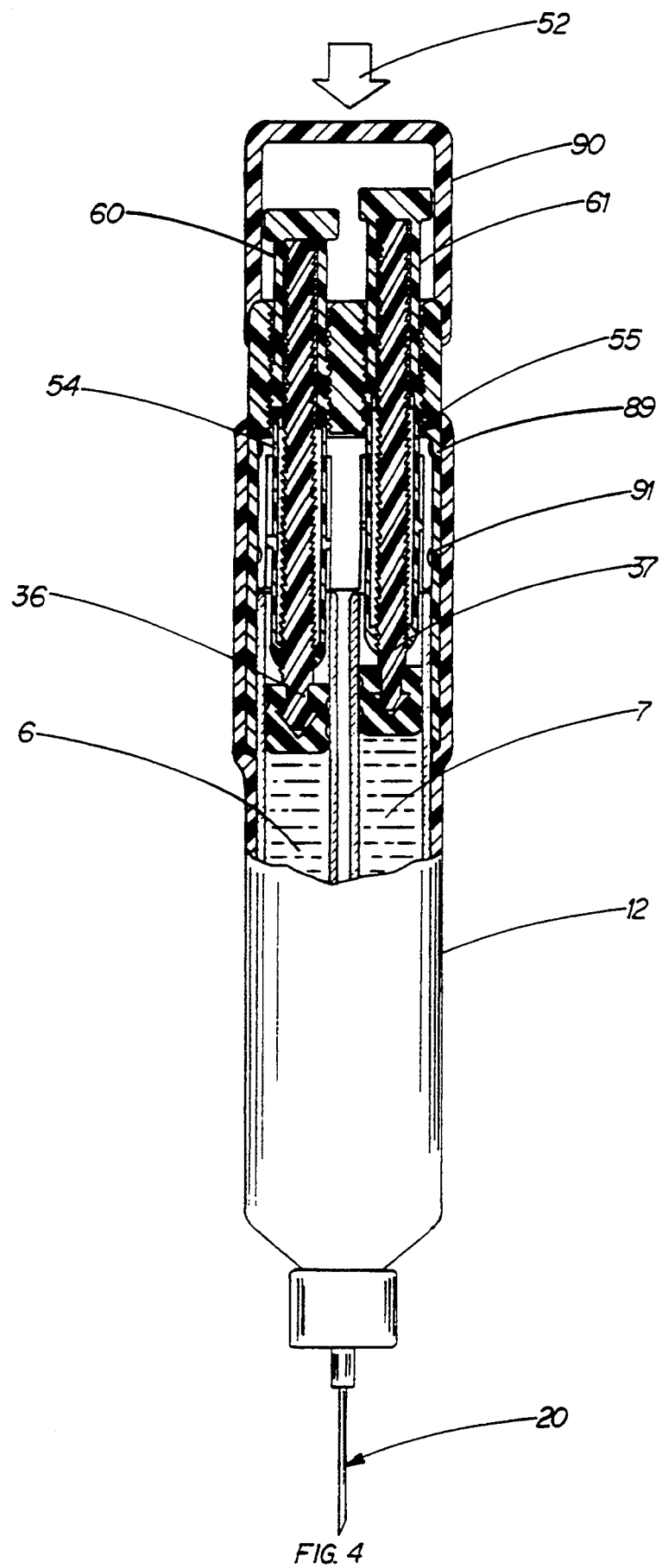
FIG. 4 shows the dispenser of FIG. 3 with the cap replaced and with the sliding body in the second, post-delivery position following dispensing of the two components in different proportions.
Figure 4A:
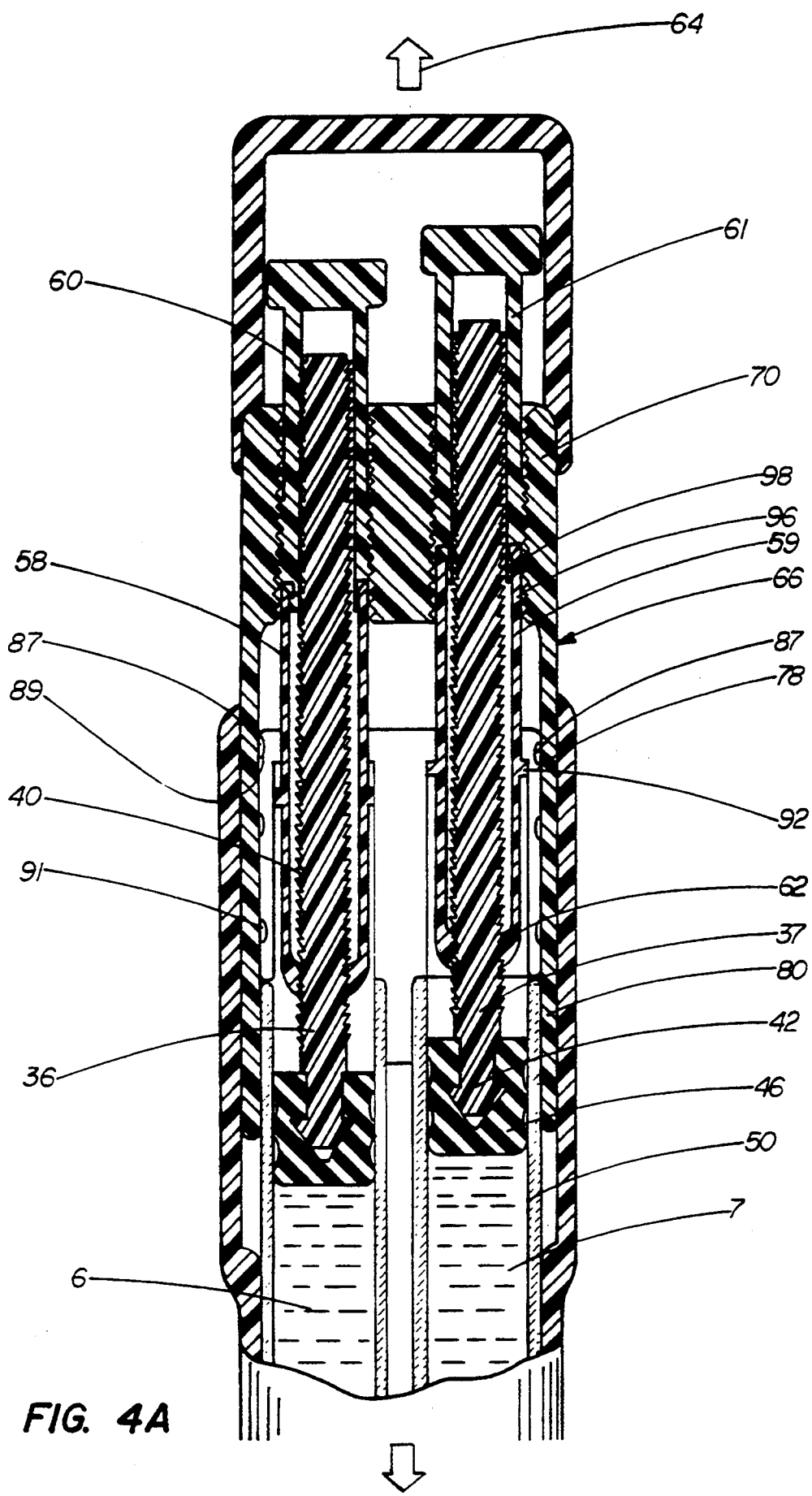
FIGS. 4A and 5 shows the dispenser of FIG. 4 with the sliding body moved from the post-delivery position of FIG. 4 to an intermediate position.

FIG. 4 shows dispenser 2 with cap 90 replaced and after reciprocating drive assembly 10 has been moved in the direction of arrow 52 during a delivery stroke from the predelivery condition of FIG. 3 to post-delivery condition of FIG. 4. Although not shown, rib 82 is in the position shown in FIG. 1 at the lower end of slot 84, rib 82 and slot 84 defining the limits of movement of drive assembly 10. Also, by comparing the positions of pistons 46 of cartridges 6, 7 it can be seen that a greater amount of the contents of cartridge 6 has been expulsed than of cartridge 7. This is due to the extra distance dosage adjuster 61 must travel before ends 96, 98 of reciprocating driver 59 and dosage adjuster 61 meet as compared with the corresponding ends of driver 58 and adjuster 60. The use of check valves 30 keep the contents of one cartridge 6, 7 from moving into the interior of the other cartridge 7, 6.

Figure 5:
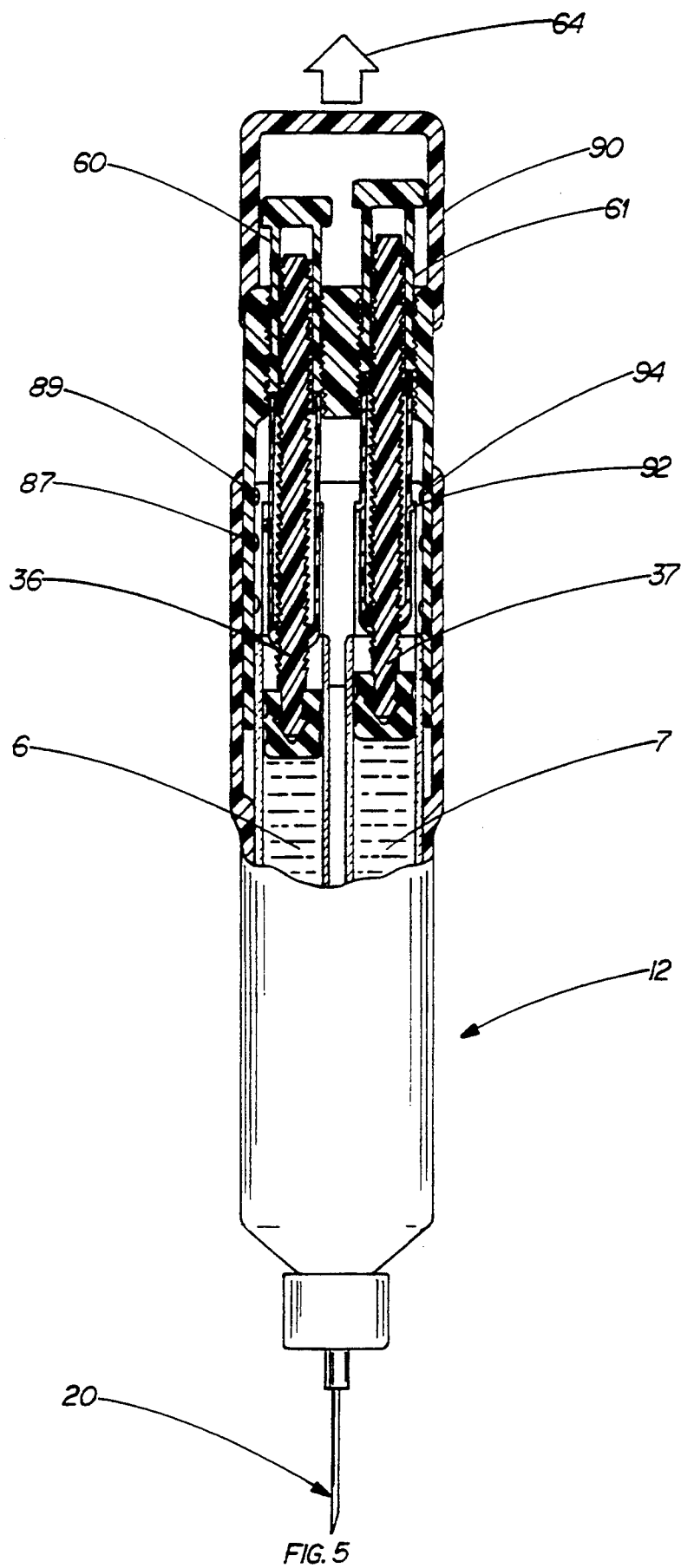

FIG. 5 illustrates variable proportion dispenser 2 with the reciprocating driver assembly 10 moved to an intermediate position between the post-delivery position of FIG. 4 by pulling in the direction of arrow 64. At this point, rib 82, not shown in FIG. 5, is mid-way along slot 84 but collar 92 of reciprocating driver 59 has engaged driver stop 94 while collar 92 of reciprocating 58 has not. Further movement of drive assembly 10 in the direction of arrow 64 will cause ends 96, 98 of one-way drive device 55 to separate as in FIG. 3. The engagement and separation of ends 96, 98 is facilitated by slits 99 in drivers 58, 59 which permit ends 96 to dilate.

To use dispenser 2, a new needle assembly 20 is generally mounted to tip 14 of housing 12. Cap 90 is removed and dosage adjusters 60, 61 are each rotated according to the amount and proportions of the contents of cartridges 6, 7 to be injected per cycle. That is, for maximum dosage, the dosage adjusters 60, 61 are kept fully engaged within threaded holes 68 to minimize the distance between ends 96, 98. Numerical indicia 100, as suggested in FIG. 1, can be used on dosage adjusters 60, 61 to permit the appropriate injection volume and proportions to be chosen. Cap 90 is then replaced onto end 70 of sliding body 66, sliding body 66 is then moved in the direction of arrow 64 so that rib 82 moves from the position of FIG. 1 at the lower end of slot 84 to the upper end of slot 84. Doing so causes stem engaging ends 62 of reciprocating drivers 58, 59 to slide over drive stems 36, 37 so that pistons 46 do not move during this return stroke. (Friction between pistons 46 and cartridges 6, 7 is sufficient to keep drive stems 36, 37 in place during the return stroke.) Sliding body 66 is then driven downwardly in a delivery stroke in the direction of arrow 52 by pressing on cap 90. The contents of cartridges 6, 7 begin to be expulsed through associated spike tips 26, 27, check valves 30, bore 16 and needle assembly 20. In the configuration of FIG. 3, a greater proportion of the contents of cartridge 6 is expulsed through needle assembly 20 than of cartridge 7 because of the relative positions of dosage adjusters 60, 61. After use, needle assembly 20 can be capped or removed and a protective cap, not shown, can be mounted to tip 14 until the next use. To give another injection with the same volume and in the same proportions, one merely replaces needle assembly 20, if required, and moves sliding body 66 in a return stroke in the direction of arrow 64 and then in a delivery stroke in the direction of arrow 52, thus repeating the process.

The present invention has been described with reference to two cartridges 6, 7. The invention may be practiced with three or more cartridges as well. Also, other types of variable volume containers instead of pharmaceutical cartridges could also be used. For example, a collapsible bellows arrangement or a collapsible bag or sack could be used instead of the cartridges. Although the outer surfaces 40 of driver stems 36, 37 are serrated or toothed to provide a good ratcheting surface, the outer surfaces could be smooth as well by using other types of one-way drivers. The present invention is shown in an embodiment in which either component can be varied over a large range, preferably a range of 0% to 100%. If desired, adjustment devices could be provided that do not give such a wide range. For example, the adjustments could be such that the percentages of the components only range from 20% to 80% rather than 0% to 100%. In the preferred embodiment both the total volume of the dosage and the proportions are adjusted using dosage adjusters 60, 61. The total volume dispensed could also be adjusted by adjusting the effective length of slot 84. In addition, one of the components could be non-adjustable so that all adjustment in proportion would be through the reciprocating drive assembly for the other component; this might be useful when a separate means for adjusting the total volume dispensed is used, such as adjusting the effective length of slot 84. Dosage adjusters 60, 61 could also be coupled to one another through different sized gears. For example, dosage adjuster 60 could have 10-tooth gear while dosage adjuster 61 could have a 6-tooth gear so that every revolution of dosage adjuster 60 would cause dosage adjuster 61 to rotate one and two-third times. This could be useful if the ratio of the components is known and only the total volume is to be changed. Of course, different sets of gears for different ratios could be provided.

FIGS. 6–8B illustrate an alternative embodiment of the invention shown in FIGS. 1–5. Dispenser 2a is similar to dispenser 2 with corresponding reference numerals referring to corresponding parts; therefore parts which are identical will not be described separately. The primary differences between dispensers 2, 2a relate to the construction of dose adjustors a, 61a, sliding body 66a and check valve 30a.

Figure 7:
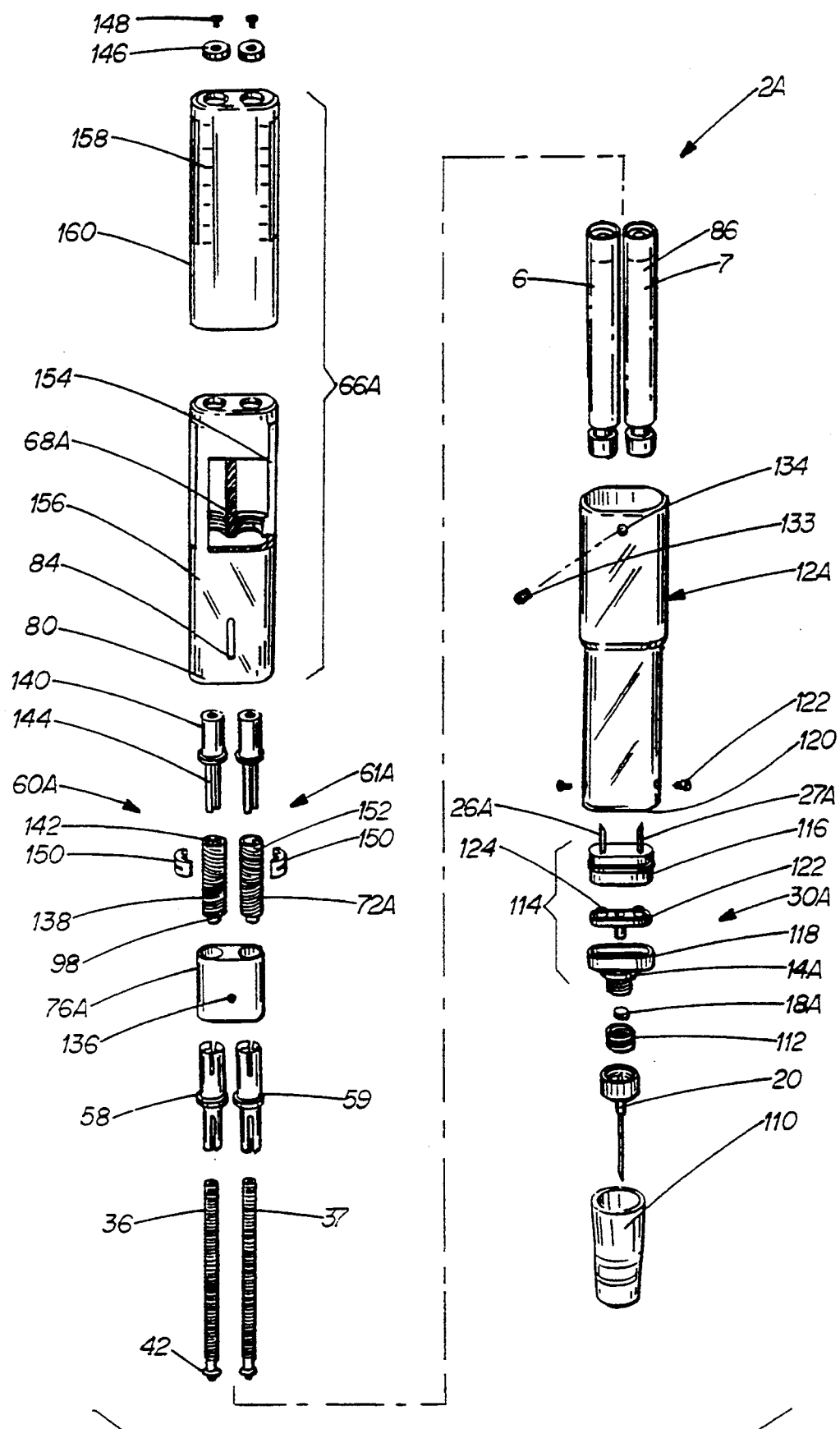
FIG. 7 is an exploded isometric view of the dispenser of FIG. 6.
Figure 8:
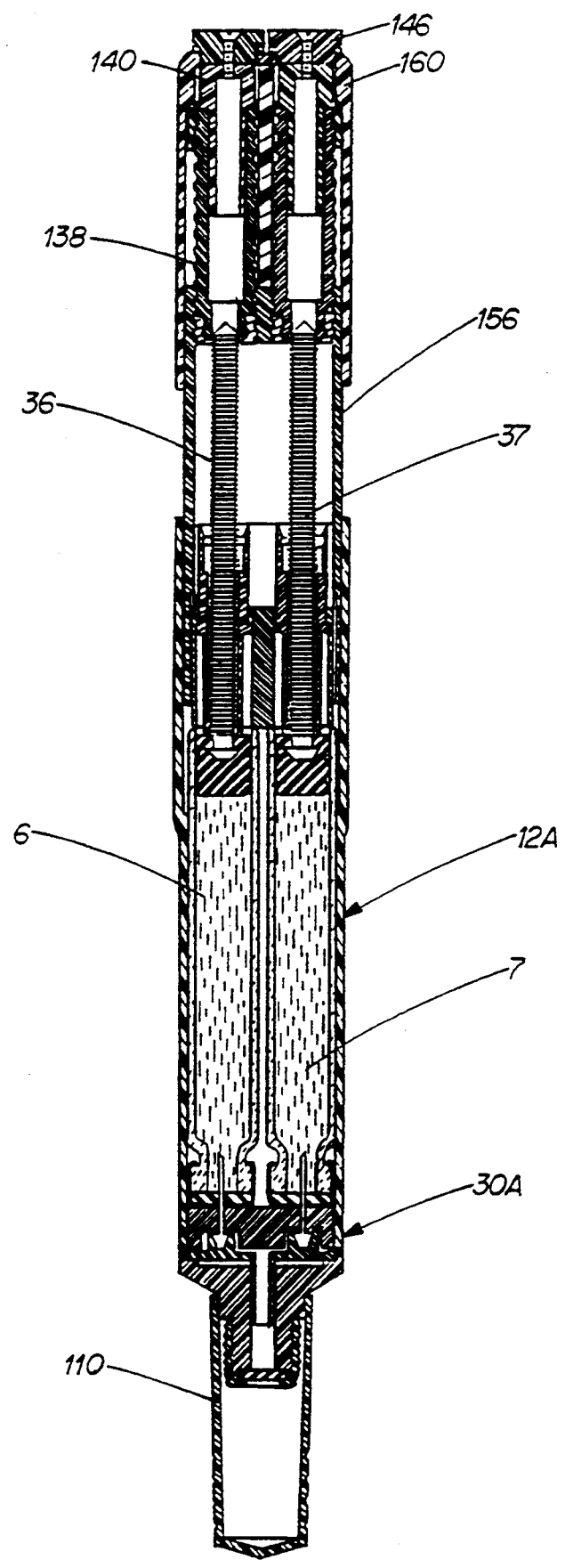
FIG. 8 is a cross-sectional view of the dispenser of FIG. 6 in the first, predelivery position.
Figure 8A:
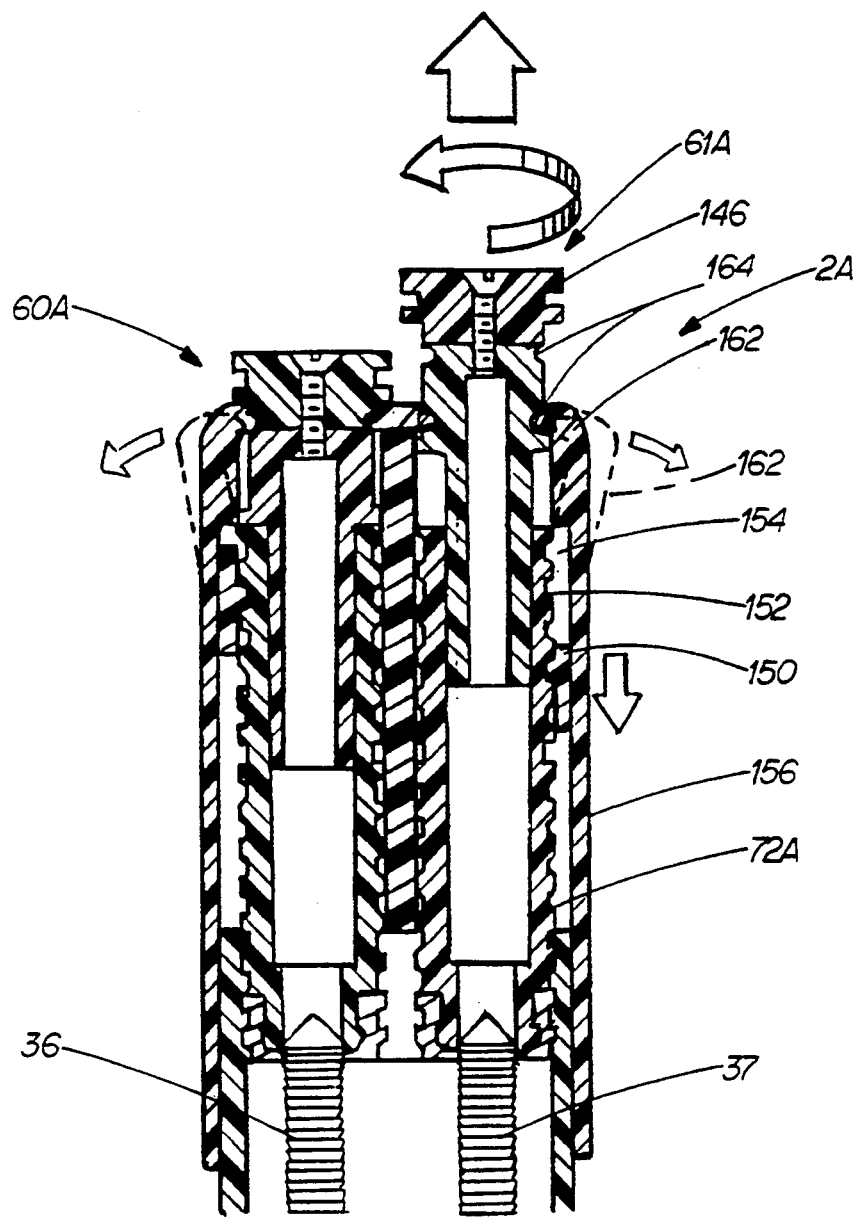
FIG. 8A is an enlarged cross-sectional view of a portion of the dispenser of FIG. 8 with the right-hand dose adjustor axially pulled away from the sliding body and after having been rotated two complete revolutions so the dose indicator has moved within the sliding body a distance equal to four pitch lengths.
Figure 8B:
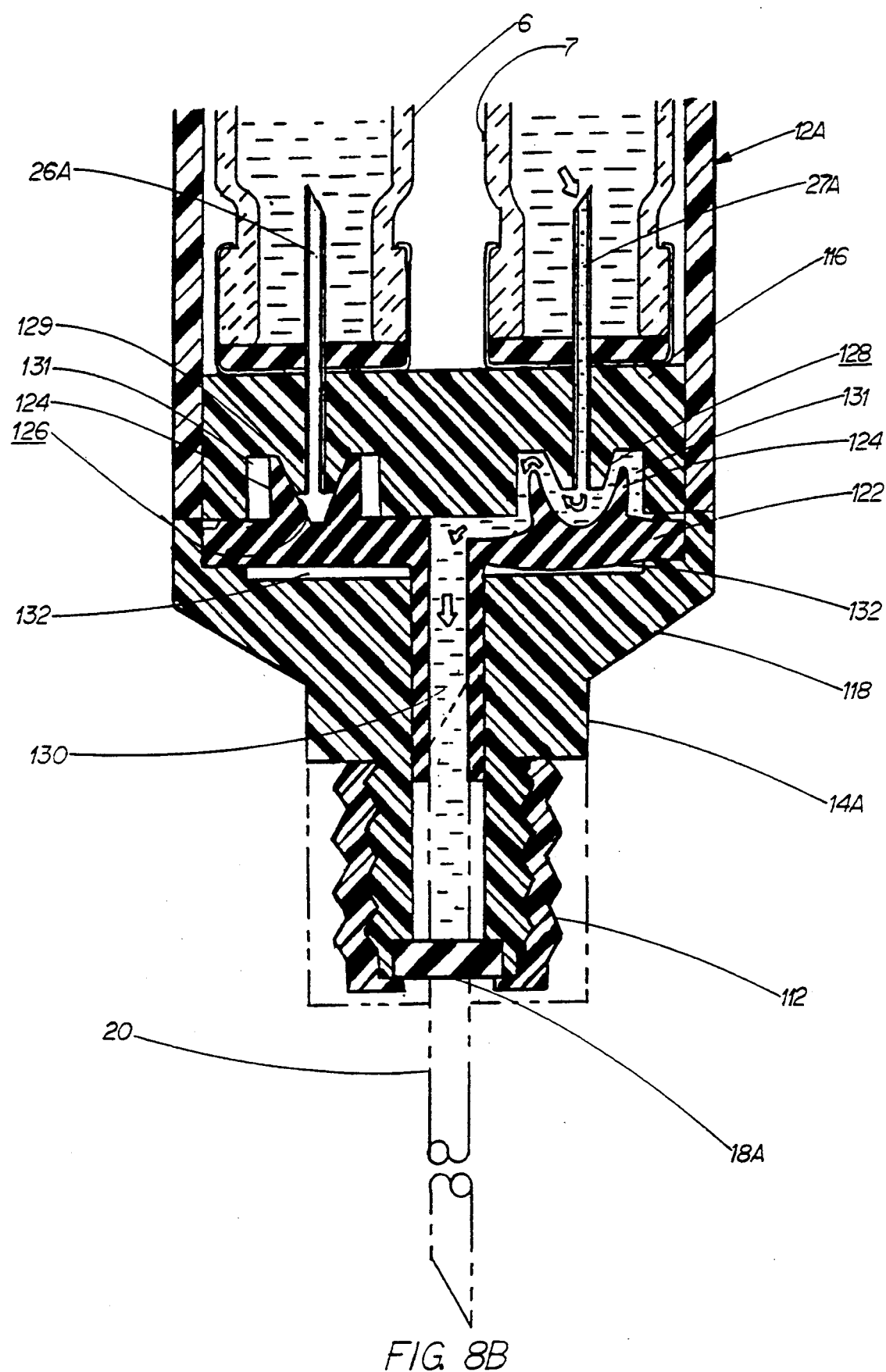
FIG. 8B is an enlarged cross-sectional view of the lower portion of the dispenser of FIG. 8 illustrating, in somewhat exaggerated form, fluid flow from the right-hand cartridge, through the spike, past the check valve, through the common passageway and into the double-ended needle shown in phantom.
Figure 9:
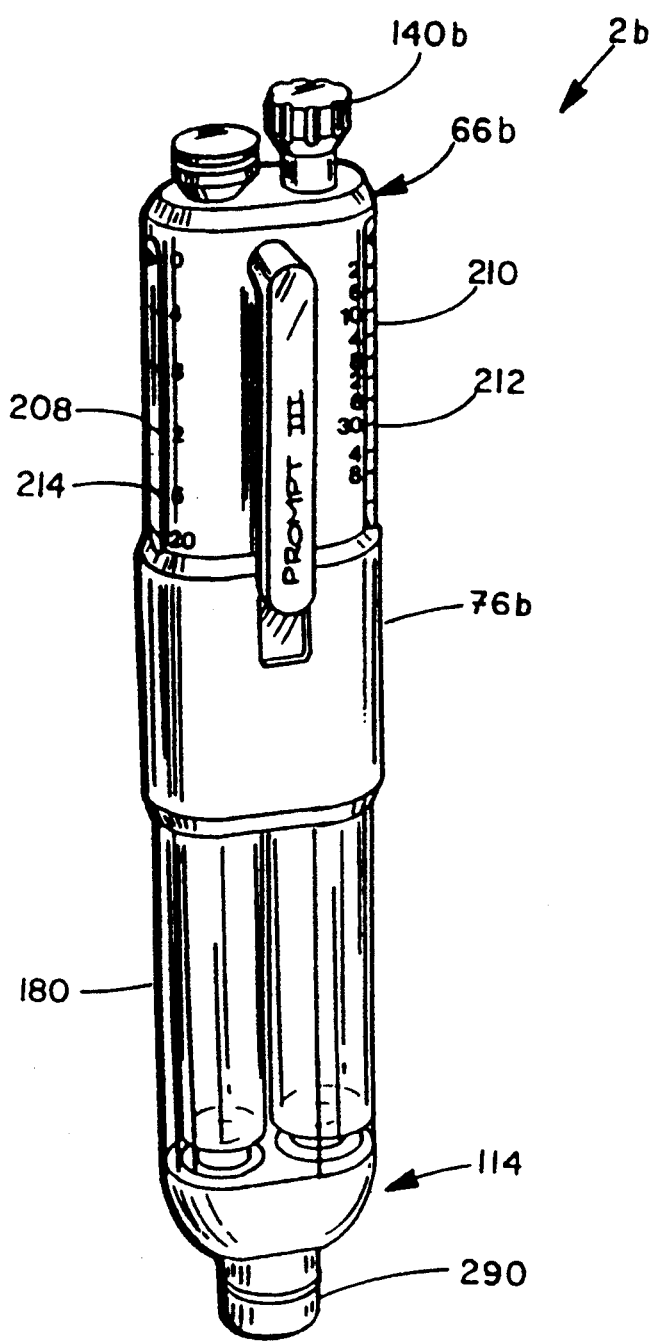
FIG. 9 is an overall isometric view of an alternative embodiment of the variable proportion dispenser shown in FIG. 6.

Referring the reader primarily to FIG. 7, a needle sheath 110 is used to cover needle assembly 20 prior to use for safety. Septum 18a, see FIGS. 8 and 8B, is kept in place on tip 18a by a threaded keeper 112. Check valves 30a are formed differently from check valves 30. A combined check valve and spike assembly 114 includes a spike adapter 116, a manifold 118 and a check valve body 122. Manifold 118 carries tip 14a and is secured to an end 120 of housing 12a, such as through the use of an adhesive. Spike adaptor 116 is mounted within the interior of housing 12a at end 120 of housing 12a and is secured thereto by the use of screws 123 as shown in FIG. 7. Check valve body 122, made from butyl rubber, is positioned between spike adaptor 116 and manifold 118, both made of a hard plastic, such as polycarbonate. Check valve body 122 includes a pair of cup-shaped members 124 each having an internal conical surface 126 positioned to engage an external conical surface 128 formed by the outside of each of two projections 129. Projections 129 are hollow, as shown in FIG. 8A, and are positioned for fluid communication with the interior of hollow spikes 26a, 27a. Together check valve body 122, spike adaptor 116 and manifold 118 combine to create check valves 30a.

Normally, as shown in the left-hand side of FIG. 8B, check valves 30a are closed preventing fluid flow from a common pathway 130, which fluidly connects to the interior of needle cannula 20, to the interior of cartridges 6, 7. However, upon pressurization of the interior of one of the cartridges, such as cartridge 7 in FIG. 8B, the corresponding check valve 30a is opened as illustrated by the deformation of check valve body 122 and the arrows indicating fluid flow in FIG. 8B. To permit this deformation, assembly 114 provides an annular gap 131 surrounding cup-shaped members 124 and a further gap 132 in the space between that portion of check valve body 122 adjacent cup-shaped members 124 and manifold 118. The deformation of check valve body 122 into both of these regions is graphically illustrated in FIG. 8B.

The configuration of assembly 114 provides a relatively short, low-volume flow path between cartridges 6, 7 and needle assembly 20. This reduces the amount of residual insulin, or other medication, left along the flow path between injections to reduce the possibility for infection.

In the embodiment of FIG. 2, limit guide 76 is secured within the interior of housing 12 by adhering rib 82, which passes through slot 84, to the interior of the housing. In contrast, dispenser 2a secures limit guide 76a to the interior of housing 12a using a set screw 133 which passes through a through hole 134 formed in housing 12a and engages a threaded hole 136 formed in limit guide 76a. Other means for securing limit guide 76a to housing 12a could be used as well.

Dose adjustors 60a, 61a are two-part members having a threaded portion 138 and a telescoping drive extension 140. Threaded portions 138 include two sets of threads. Threads 72a are right-hand threads and engage internally threaded holes 68a in sliding body 66a for the same reasons and in the same manner as external threads 72 engage threaded holes 68 in the embodiment of FIG. 2. Threaded portion 138 has an oblong bore 142 sized to accept a similarly shaped oblong extension 144 of extension 140. The interface between bore 142 and extension 144 permits the free telescoping movement of extension 144 within bore 142 but causes rotary motion applied to extension 140 to rotate threaded portion 138.

Figure 6:
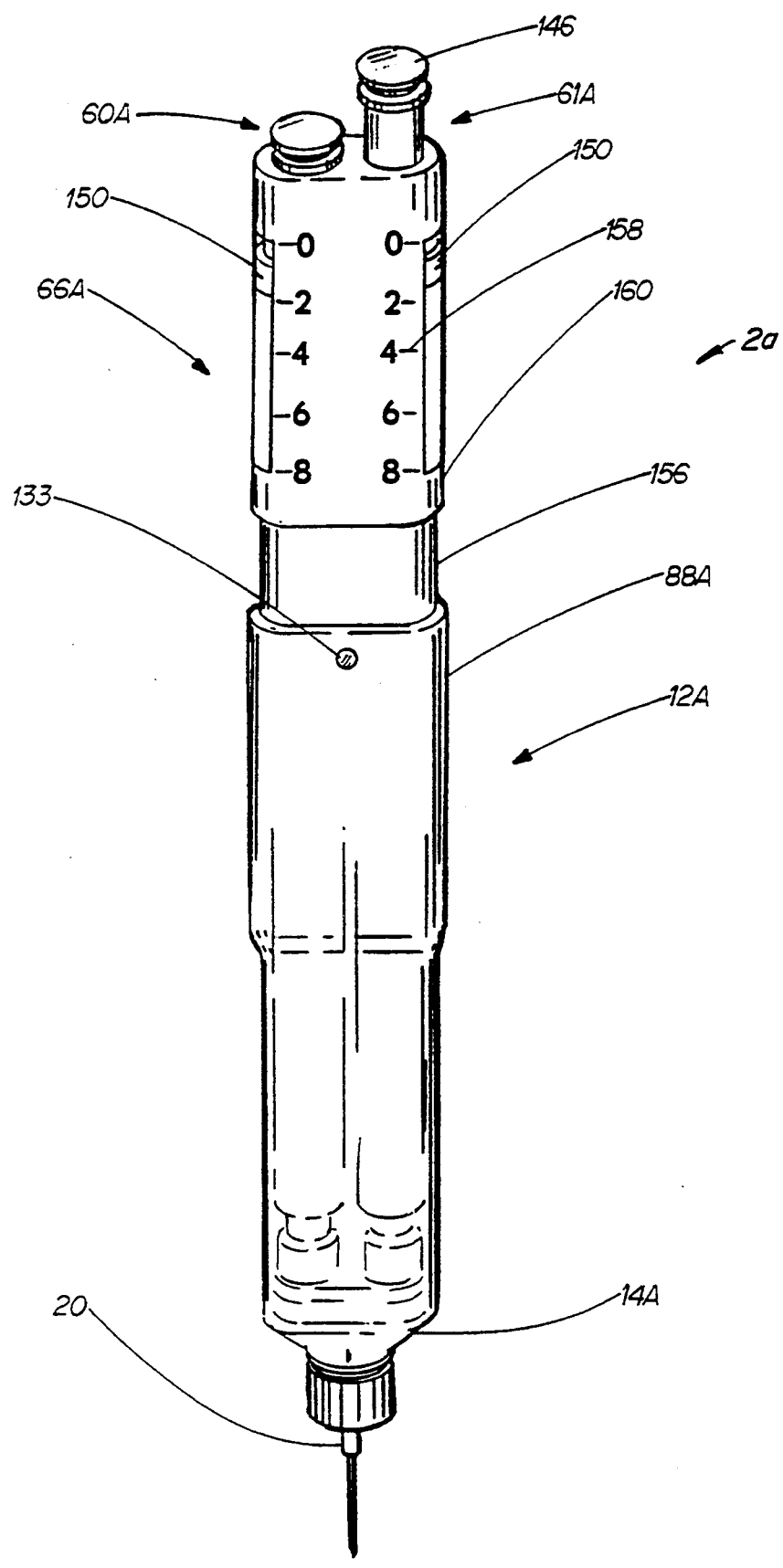
FIG. 6 is an overall isometric view of an alternative embodiment of the variable proportion dispenser shown in FIG. 1 in the first, pre-delivery position with a dosing control knob pulled out away from the sliding body to facilitate adjustment.

As shown in FIG. 6, dose adjustor 60a also includes a dose control knob 146 which is secured to the end of extension 140 by a screw 148. Knob 146 can be grasped by a user and pulled away from sliding body 66a. Doing so permits the user to easily and independently rotate either dose adjustor 60a, 61a as desired without inadvertently rotating the other dose adjustor. For example, in FIGS. 6 and 8A, dose knob 146 of dose adjustor 61a has been pulled away from sliding body 66a to permit the free rotation of the dose adjustor.

Rotation of dose knob 146, in addition to moving threaded portion 138 within sliding body 66a through the engagement of threads 72a and 68a, also causes the movement of a dose indicator 150. Dose indicator 150 engages left-hand threads 152 formed at the end of threaded portion 138 opposite right-hand threads 72a. Dose indicator 150 rides within a cutout 154 formed in the inner part 156 of sliding body 66a. Sliding body 66a also includes a transparent outer part 160, which carries indicator markings 158, mounted over and secured to inner part 156, such as with an adhesive. Cutout 154 keeps dose indicator 150 from moving in a rotary direction while allowing dose indicator 150 to be moved axially. In the preferred embodiment the pitch for threads 72a and 152 is the same. Accordingly, rotating dose knob 146 one complete revolution causes threaded portion 138 to move axially within sliding body 66a one pitch length of threads 72a. However, dose indicator 150, which engages left-hand threads 152 also moves one pitch length along threads 152. Thus, rotating dose knob 146 in a clockwise direction as indicated in FIG. 8A drives threaded portion 138 downwardly in the figure thus carrying dose indicator 150 with it. In addition to this movement, dose indicator 150 is moved one pitch length due to its engagement of the left-hand threads 152. This causes dose indicator 150 to move twice the distance traveled by threaded portion 138 and thus twice the distance travelled by drive stem 37. This magnifies the distance between indicator markings 158 by a two to one margin.

FIG. 8A illustrates dispenser 2a after dose knob 148 of dose adjustor 61a has been pulled outwardly to its operating position. Outer part 160 has a pair of spring fingers 162 formed at its upper end which engage grooves 164 formed in extensions 140. Spring fingers 162 and grooves 164 creates detents which provide a positive indication to the user when dose adjustors 60a, 61a are in the retracted or extended positions. It should be noted that the axial movement of dose knob 148 together with extension 140 does not affect the operation of the unit; it only permits the appropriate dose adjustor to be rotated without affecting the rotary position, and thus the dose associated with the rotary position, of the other dose adjustor. If desired, the detents could be made so that the outermost groove 164 includes a series of notches while the innermost groove 164 is smooth so that, with reference to FIG. 8A, rotary motion of dose adjustor 61a is relatively unrestricted while rotary motion of dose adjustor 60a is substantially hindered or prevented.

FIGS. 9–18B illustrate an alternative embodiment of the inventions shown in FIGS. 1–8B. Dispenser 2b is similar to dispenser 2a with corresponding reference numerals referring to corresponding parts. Parts which are identical are therefore not described separately.

Figure 10:
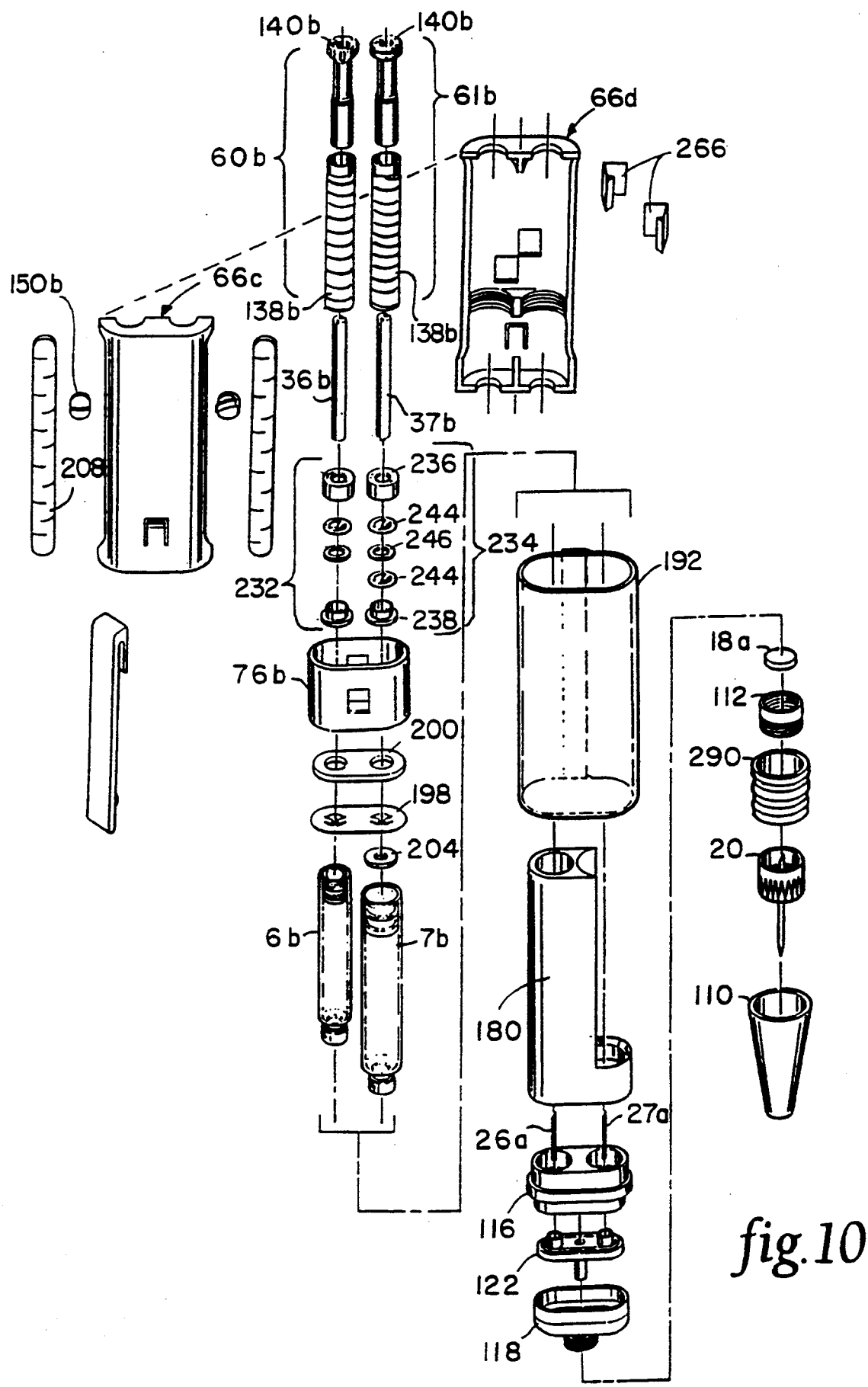
FIG. 10 is an exploded isometric view of the dispenser of FIG. 9 with a needle assembly and needle sheath added.
Figure 10A:
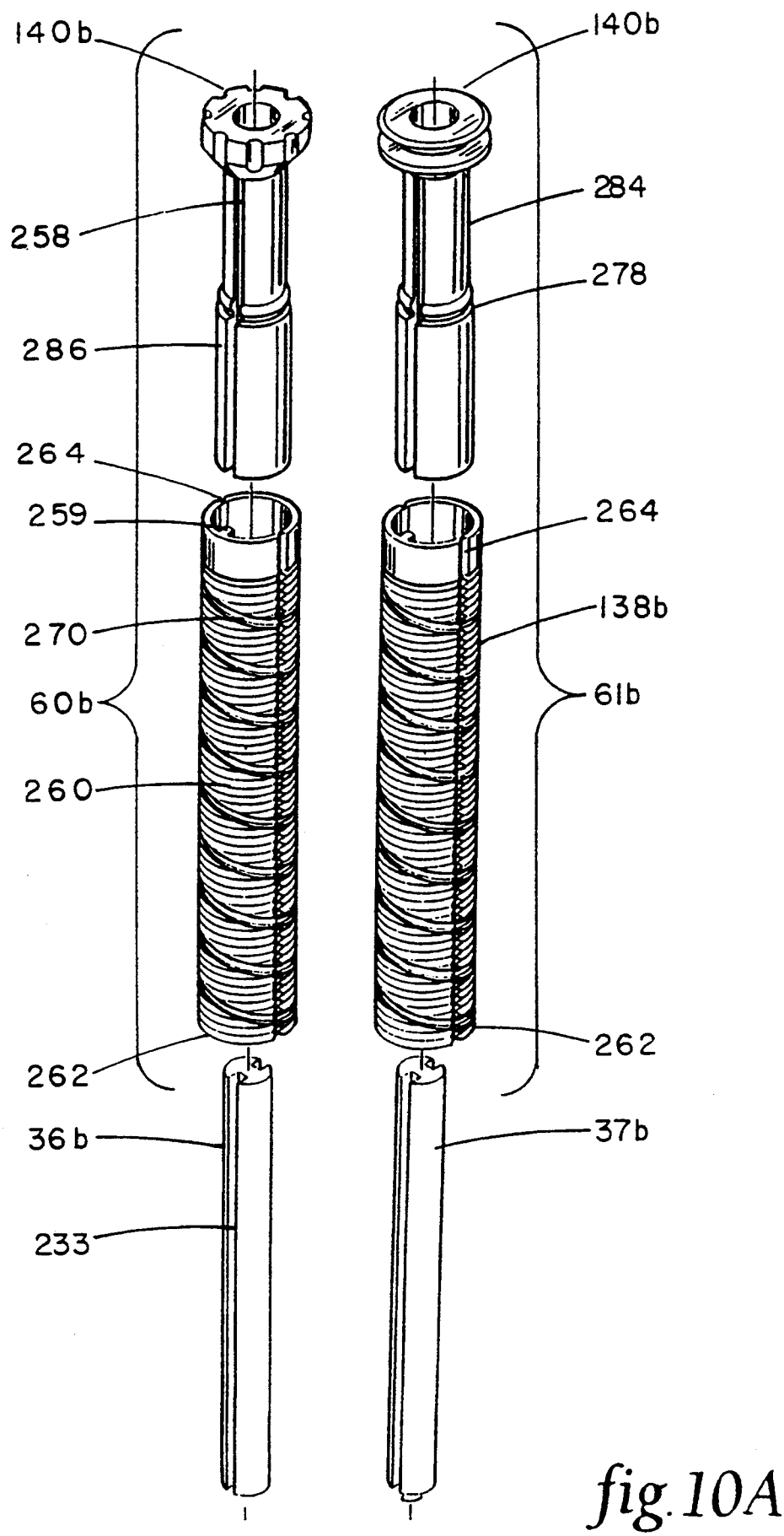
Figure 10B:
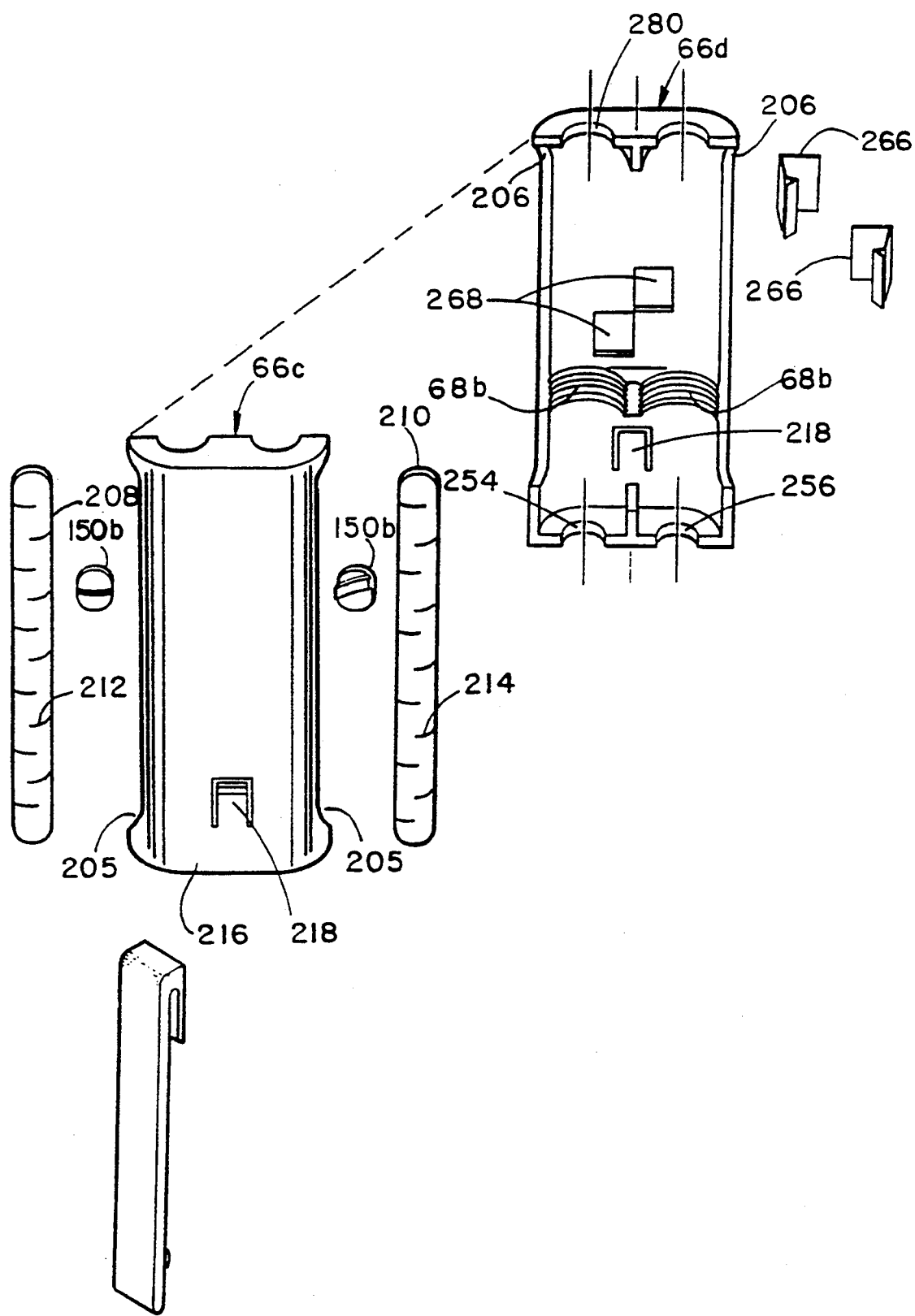
Figure 10C:
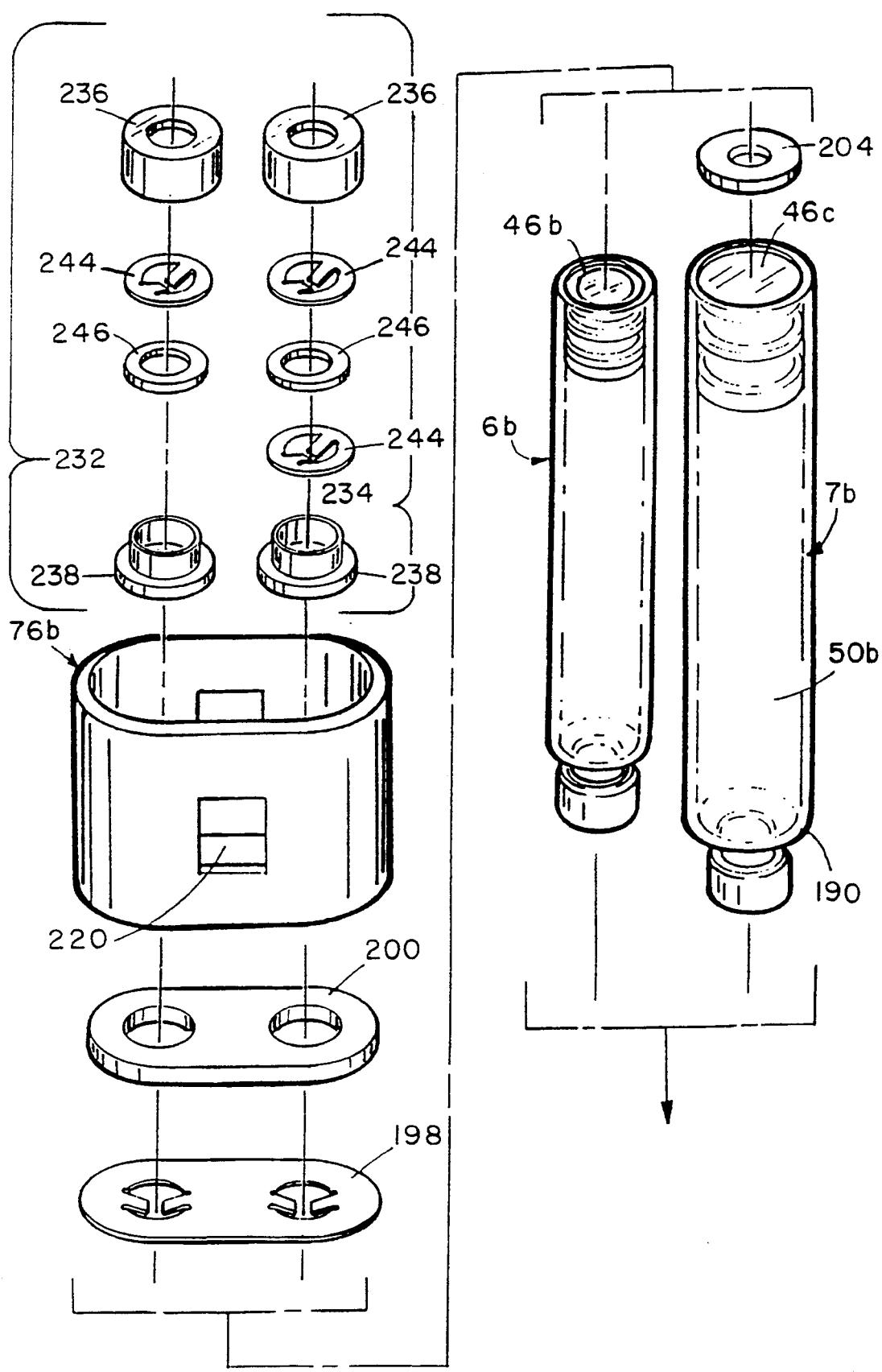
Figure 10D:
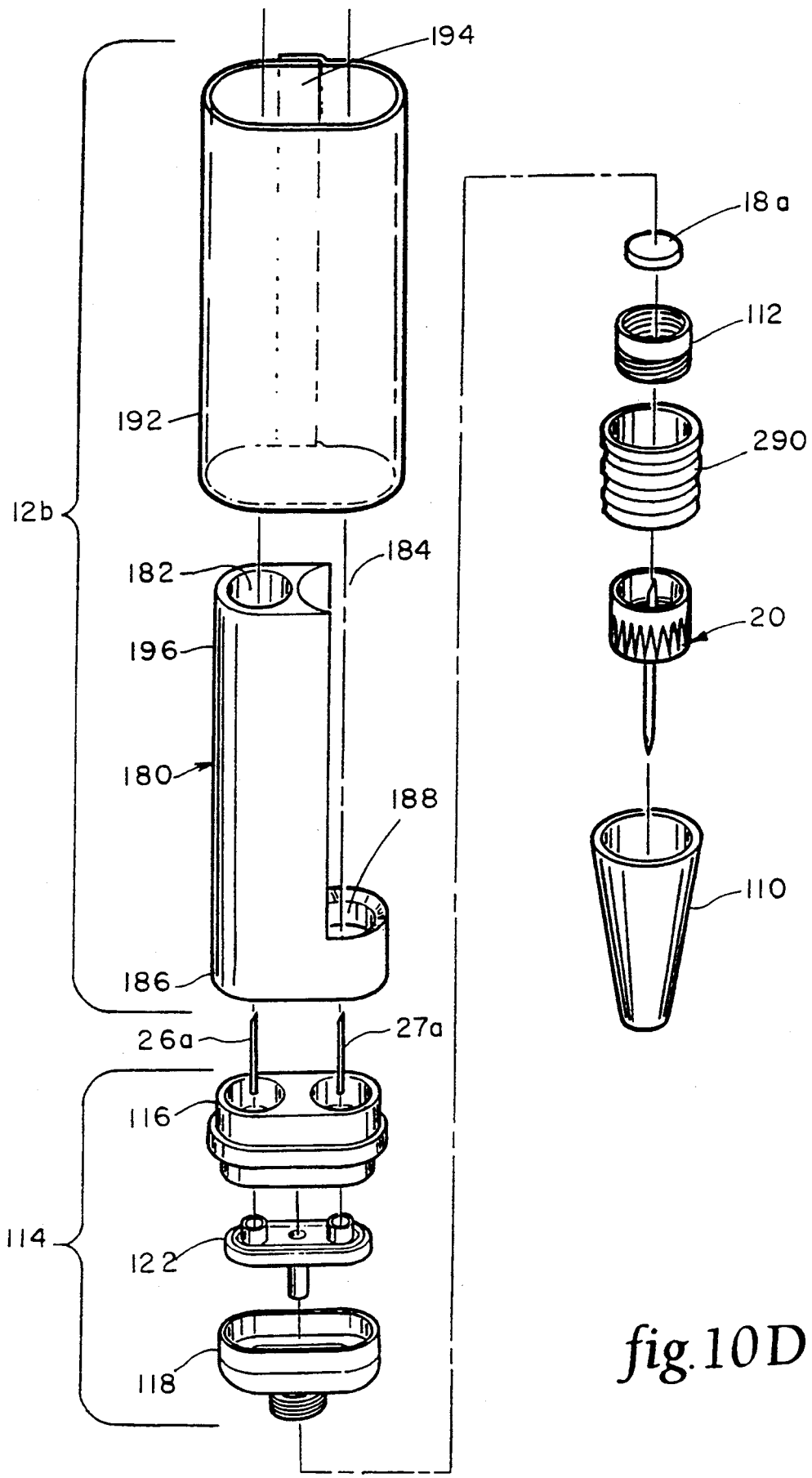

FIG. 10 shows that housing 12b is sized to accommodate two different size cartridges 6b, 7b. In the embodiment disclosed in FIG. 10, cartridges 6b, 7b are 1.5 ml and 3 ml, respectively. Each unit of medicine is equal to 0.01 ml so that cartridge 7b contains 300 units of medication. The lengths of cartridges 6b, 7b are about the same: cartridge 7b is about 0.20 inch (5.08 mm) longer than cartridge 6a. Therefore, moving piston 46b of cartridge 6b and piston 46c of cartridge 7b the same axial distance will cause about twice as much of the medication from cartridge 7b to be dispensed as from cartridge 6b. Thus, dispenser 2b helps accommodate those situations in which one pharmaceutical is used in greater proportion than the other pharmaceutical, in this case about a two to one proportion. Of course other proportions can be used as well; this helps to prevent situations in which one cartridge is depleted while the other cartridge is still, for example, half full.

To help minimize the thickness of dispenser 2b, housing 12b includes a rigid base 180 having a bore 182 sized to accommodate cartridge 6b and a semi-cylindrical cutout 184 sized to partially house barrel 50b of cartridge 7b. The lower end 186 of cutout 184 has a cylindrical opening 188 to house the septum end 190 of cartridge 7b. Housing 12b also includes a clear plastic retaining wrap 192 made of, for example, vinyl or mylar, which is wrapped around base 180 housing cartridges 6b, 7b therein. Wrap 192 is secured to itself along an overlap region 194, such as by ultrasonic welding techniques. In this manner, the thickness of housing 12 and thus dispenser 2b is minimized. If for some reason additional protection or strength is needed, housing 12b could be created similar to housing 12a with material surrounding the entire length of both cartridges 6b and 7b.

One of the main differences between dispensers 2b and 2a is that dispenser 2b uses drive stems 36b, 37b which are smooth along their axial lengths as opposed to ratchet surface drive stems 36, 37. This permits very precise increments of medication to be metered. That is, the axial movement of the drive stems are not limited to certain finite increments as are drive stems 36, 37 which include serrations.

Figure 11:
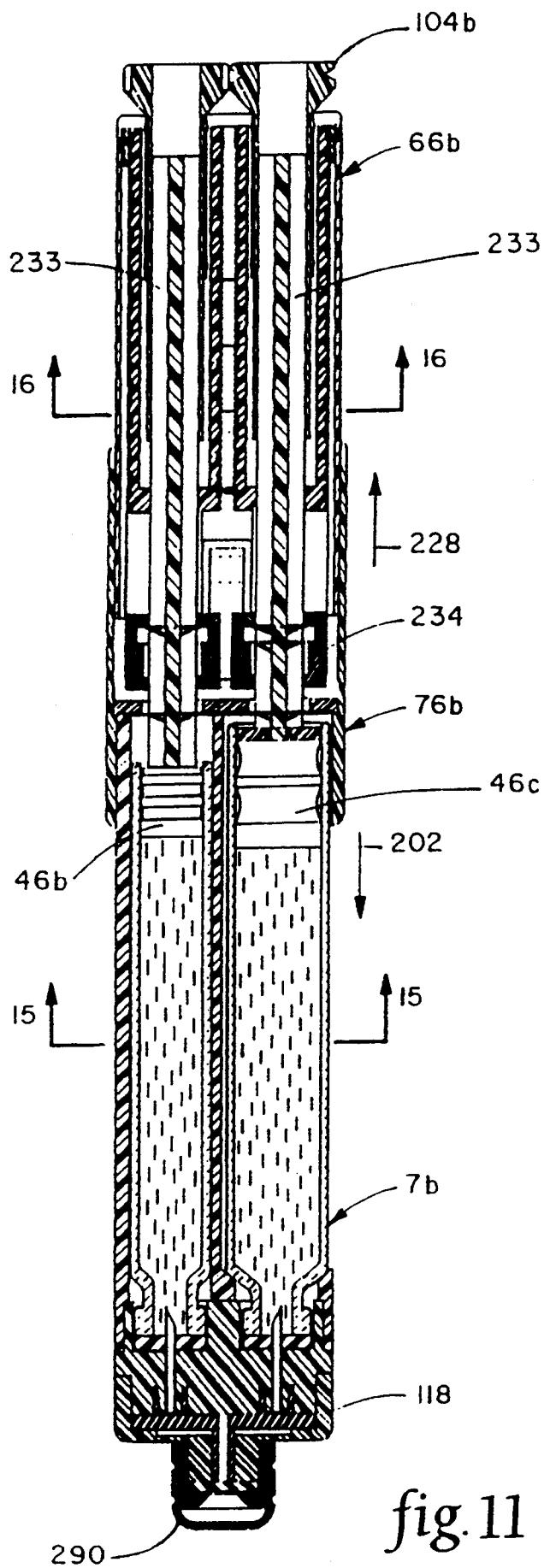
FIG. 11 is a cross-sectional view of the dispenser of FIG. 9 with the telescoping drive extension of the right-hand dose adjuster retracted from the extended position of FIG. 9.
Figure 12:
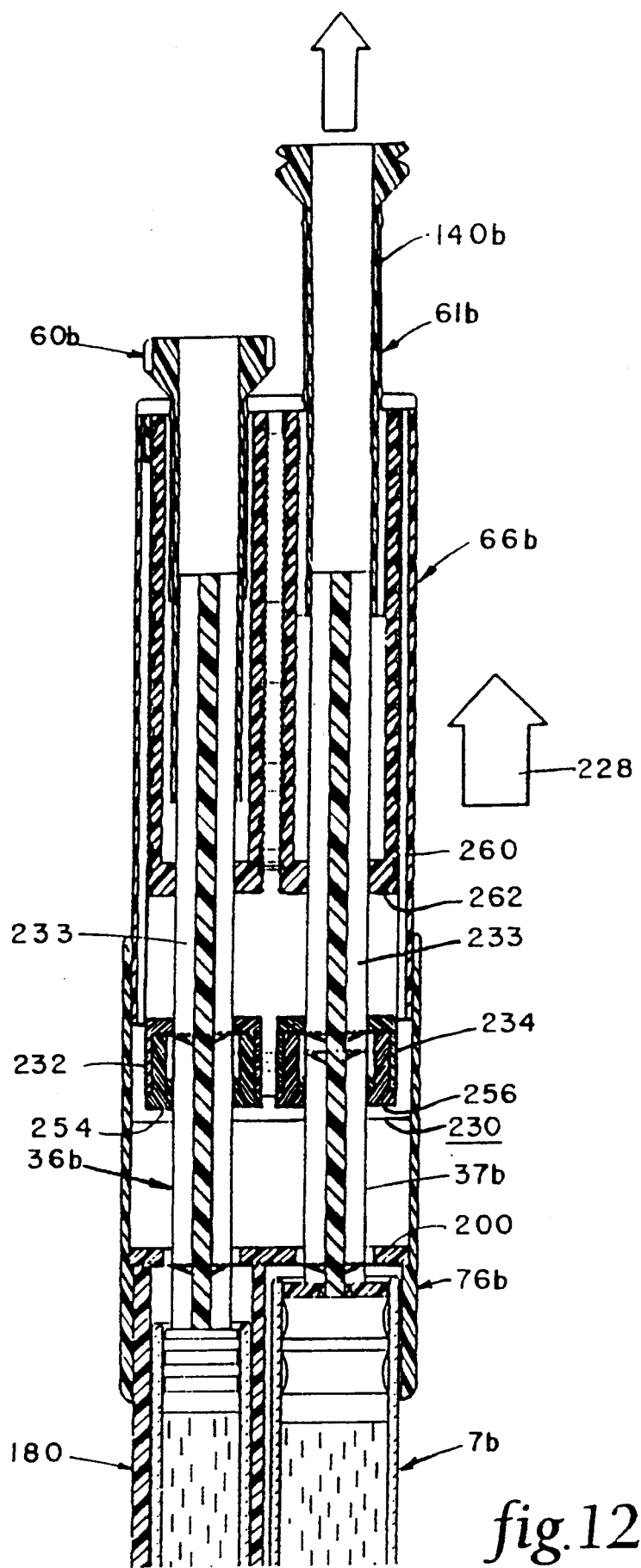
FIG. 12 is an enlarged partial cross-sectional view of the dispenser of FIG. 11 with the drive extension of the right-hand dose adjuster fully extended.

Referring now also to FIGS. 11 and 12, a limit guide 76b is shown secured, such as through the use of an adhesive or other bonding techniques, to the upper end 196 of base 180. A distal rachet plate 198 is secured within limit guide 76b and against upper end 196 of base 180 by a retaining plate 200. Accordingly, base 180, rachet plate 198, retainer plate 200 and limit guide 76b are all secured to one another and do not move relative to one another during use. Rachet plate 198 is configured to permit drive stems 36b, 37b to move distally, that is in the direction of arrow 202 in FIG. 11, but not the reverse. Since drive stems 36b, 37b do not have an enlarged distal end, a drive disk 204 is positioned between rachet plate 198 and piston 46c to better distribute the force from the drive stem 37b to piston 46c. The difference in size between piston 46b and guide stem 36b is not considered sufficiently large to require a drive disk for it. However, a drive disk could be used adjacent piston 46b if desired.

Sliding body 66b is seen to include a first sliding body half 66c and a second sliding body half 66d. Halves 66c, 66d include cutouts 205, 206 within which their clear plastic dose indicator viewing windows 208, 210 are mounted when halves 66c, 66d are assembled. Windows 208, 210 have markings 212, 214 along their lengths to provide a user with a visual indication of the dose for that particular component according to the locations of dose indicators 150b, 150c. This will be described in more detail below.

The distal end 216 of sliding body 66b is housed within limit guide 76b. Sliding body halves 66c, 66d each have an outwardly biased spring tab 218 positioned to engage a similarly positioned opening 220 formed in limit guide 76b. The use of spring tabs 218 permit end 216 of sliding body 66d to be inserted into limit guide 76b due to the inward flexing of spring tab 218 as shown in dashed lines in FIG. 17. The axial movement of sliding body 66b is seen from FIG. 17 as being equal to the distance 222 between the proximal ends 224 of openings 220 and opposed surfaces 226 of spring tabs 218. Movement of sliding body 66b in a proximal direction, that is in the direction of arrow 228, is halted by engagement of surface 226 with proximal end 224 of opening 220; movement in the distal direction of arrow 202 is halted by the engagement of end surface 230 (see FIG. 12) at distal end 216 of sliding body 66b, with retainer plate 200, seen best in FIGS. 14 and 17.

The first and second proximal rachet assemblies 232, 234 (see FIG. 10) are used to permit drive stems 36b, 37b to move in the distal direction of arrow 202 but not in the proximal direction of arrow 228 (see FIG. 11). Assemblies 232, 234 each include a proximal collar half 236 and a distal collar half 238, which combine and constitute first and second collars. When assembled, the collars each house a first rachet disk 244, shown in more detail in FIGS. 18–18B, and a spacer 246. Rachet disk 244 includes an annular periphery 248 and a pair of angled fingers 250. Rachet disks 244 are preferably made of spring stainless steel and are similar to fasteners used as push-on fasteners over a stud. Drive stems 36b, 37b have axially extending grooves 233, shown best in FIG. 16, which define smooth drive surfaces 235 against which fingers 250 press. The gap 252 between fingers 250 is somewhat less than the distance between drive surfaces 235 of drive stems 36b, 37b. The angle, spacing and resiliency of fingers 250 permit drive stems 36b, 37b to move in the distal direction of arrow 202 but not the reverse. Two ratchet disks 244 are used with assembly 234 due to the larger diameter of cartridge 7b over the diameter of cartridge 6b and the increased force required to move piston 46c over that required for piston 46b. Rachet assemblies 232, 234 are secured within sliding body 66b at distal end 216 against circular ledges 254, 256 so that rachet assemblies 232,234 move with sliding body 66c and act as one-way drivers of drive stems 36b, 37b.

Figure 16:
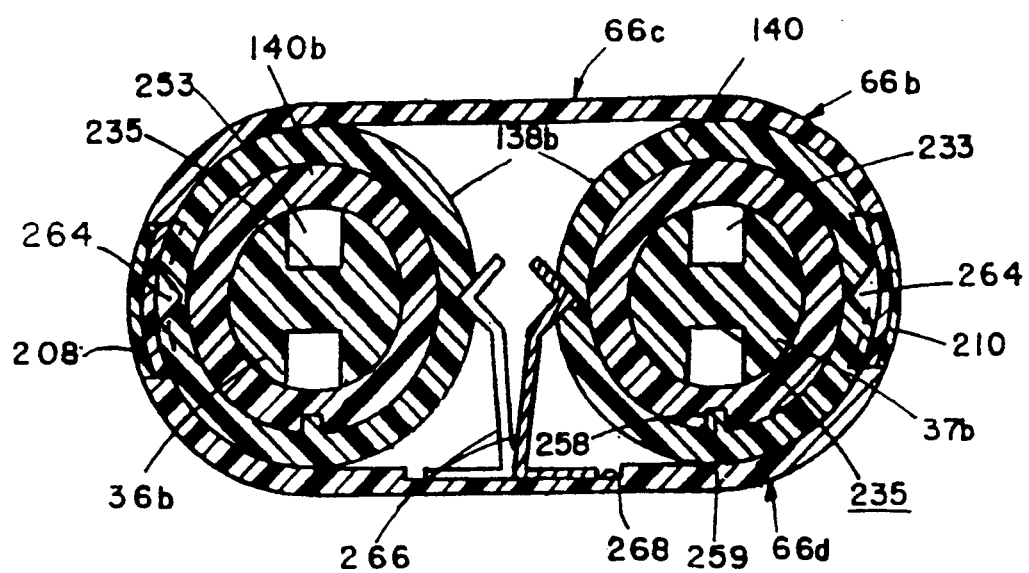
FIG. 16 is a cross-sectional view taken along line 16—16 of FIG. 11 illustrating the engagement of the detent springs with one of the axial grooves formed in the threaded portions of the dosage adjusters to provide the user with an aural and tactile indication of each half revolution of the dosage adjusters.
Figure 17:
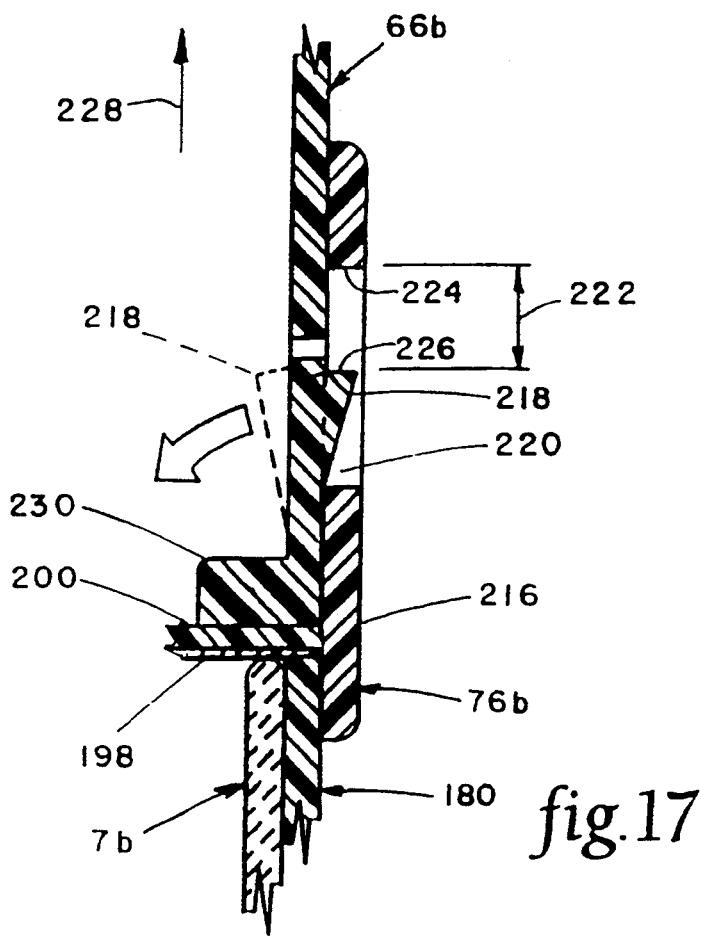
FIG. 17 is an enlarged partial cross-sectional view through the guide sleeve taken in a direction perpendicular to the cross-sectional view of FIG. 14.
Figure 18:
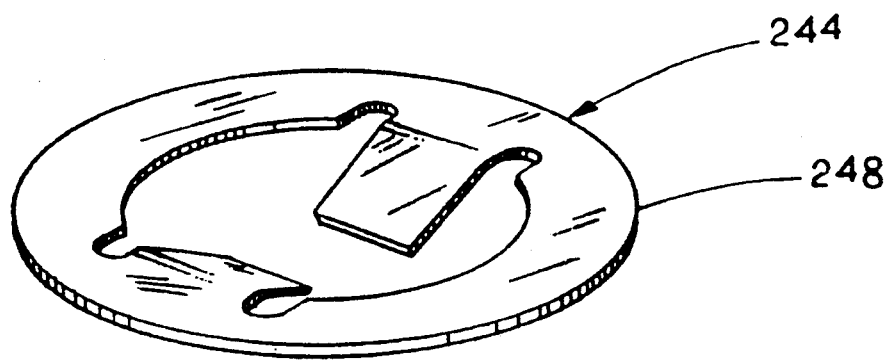
FIGS. 18, 18A and 18B are isometric, top and side views of the rachet disk shown in FIG. 10.
Figure 18A:
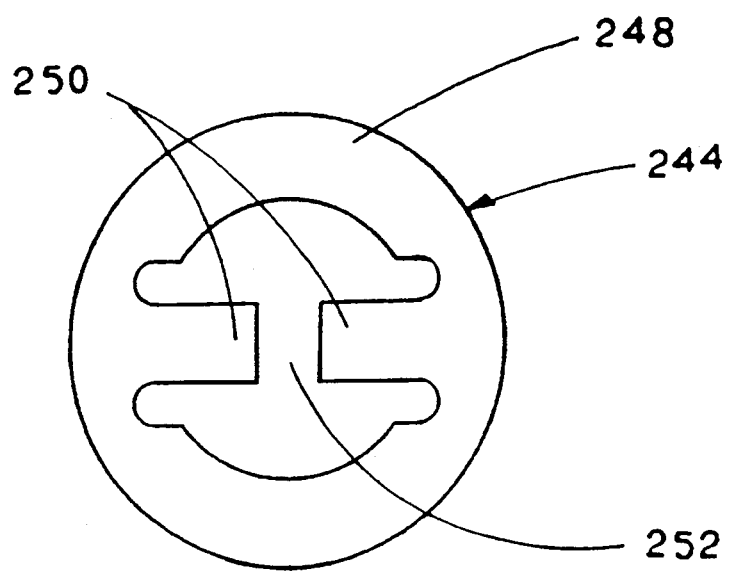
Figure 18B:
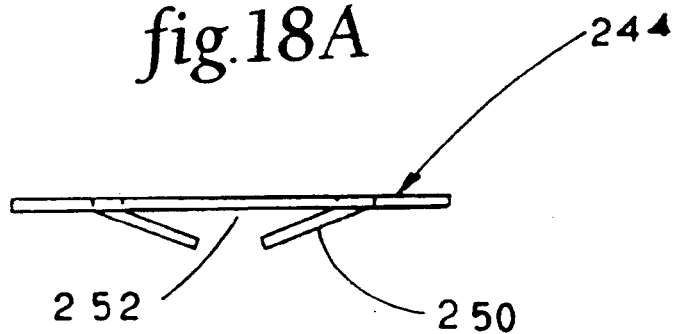

Dose adjusters 60b, 61b include threaded portions 138b and telescoping drive extensions 140b. Extensions 140b, as shown in FIG. 16, have axial grooves 258 while threaded portions 138b have complementary axial splines 259 to permit drive extensions 140b to telescope, that is move axially within threaded portions 138b, but permit rotary motion to be imparted to threaded portions 138b by the rotation of drive extensions 140b. Threaded portions 138b have two sets of threads formed on their outer surfaces over their entire lengths. The first set of threads 260 are relatively shallow right-hand threads with, in the preferred embodiment, 46 threads per inch. One-half of a revolution will cause the threaded portion 138b to move about 0.011 inch (0.28 mm). By reviewing FIGS. 12, 13 and 14, it is seen that proximal rachet assemblies 232, 234 slide along drive stems 36b, 37b and are captured between circular ledges 254, 256 (see FIGS. 10, 12) at distal end 216 of sliding body 66b at one extreme and by the distal ends 262 of threaded portions 138b at the opposite extreme. Sliding body halves 66c, 66d have internally threaded holes 68b with which right-hand threads 260 engage. Accordingly, rotating drive extension 140b in the clockwise direction as suggested in FIG. 13 causes threaded portion 138b of dose adjuster 61b to move distally in the direction of arrow 202 thus causing distal end 262 of threaded portion 138b of dose adjuster 61b to move towards proximal rachet assembly 234.

Threaded portion 238b has two grooves 264 spaced 180° apart which are engaged by detent springs 266 as shown in FIG. 16. Detent springs 266 are positioned within sliding body 66b and are fixed within pockets 268 using a suitable adhesive. Detent springs 266 are made of a metallic spring material, such as spring quality stainless steel. Detent springs 266 provide both an audible and tactile indication to the user for each one-half revolution of telescoping drive extension 140b. The preferred embodiment uses 46 threads per inch for right-hand threads 260 for both dose adjusters 60b and 61b ; however, dose adjusters 60b and 61b could be made with different numbers of threads per inch.

Threaded portions 138b also have on their outer surfaces relatively deep left-hand threads 270 formed over and coextensive with right-hand threads 260. Left-hand threads 270 have, in the preferred embodiment, a pitch of 7¾ threads per inch (3.05 threads per cm). This creates a pitch of about 0.065" (1.64 mm) for left-hand threads 270. Dose indicators 150b are housed within slots 204, 205 adjacent dose indicator viewing windows 212 and engage left-hand threads 270. Accordingly, for each one-half revolution of threaded portions 138b, dose indicators 150b, 150c will each move a distance equal to the sum of the axial movement of its associated threaded portion 138b plus the movement of dose indicator 150b, 150c along left-hand thread 270 for a total axial movement of about 0.075" (1.9 mm). Accordingly, dose indicators 150b, 150c are provided with about a seven fold increase in distance travelled over that which would be obtained merely through the axial movement of threaded portions 138b. This magnified movement of dose indicators 150, preferably at least by a factor of two, greatly helps the user to select the correct dose.

Figure 13:
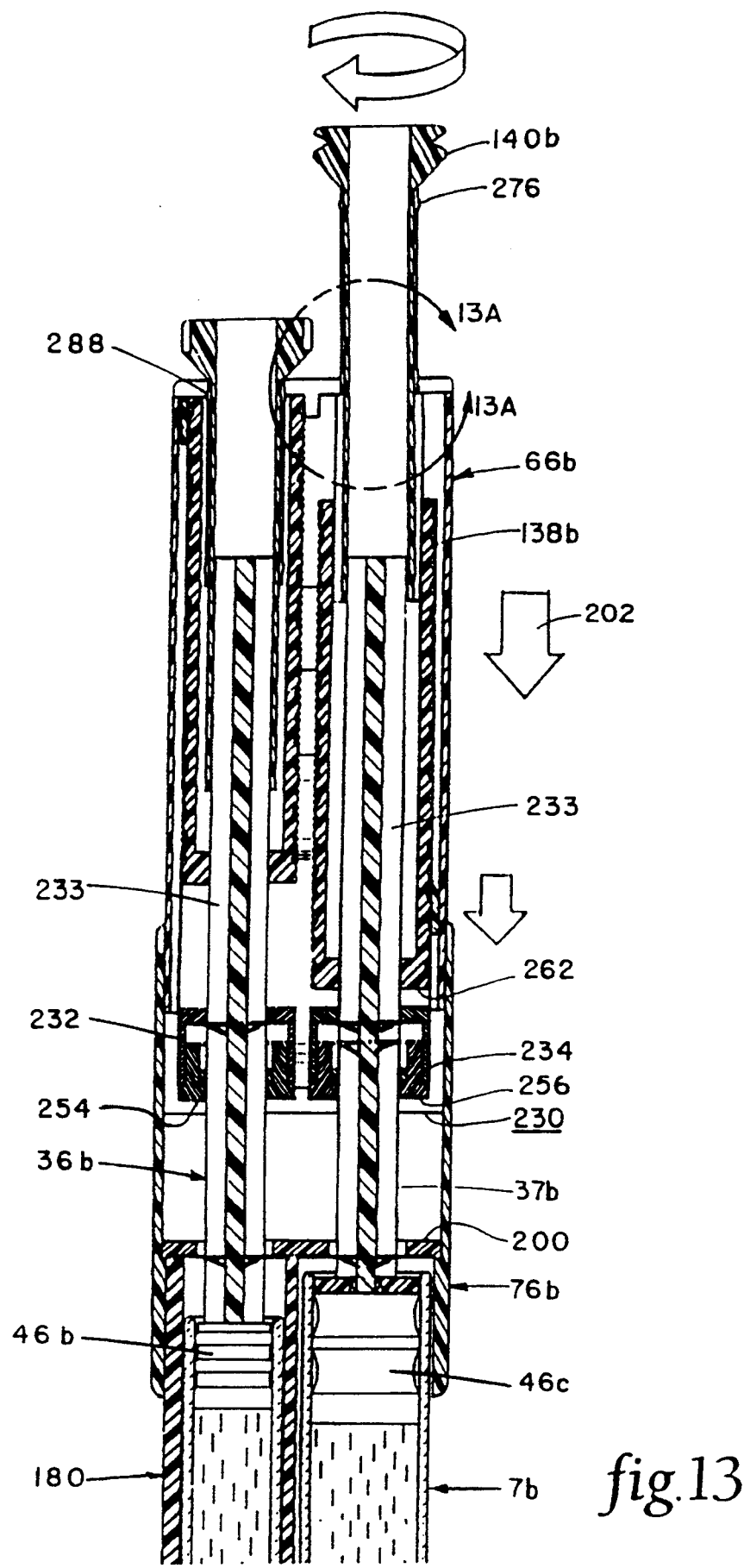
FIG. 13 shows the dispenser of FIG. 12 after the drive extension of the right-hand dose adjuster has been rotated in a clockwise direction as indicated by the arrow thus forcing the threaded portion of the dose adjuster to move downwardly or distally towards the cartridge.
Figure 13A:
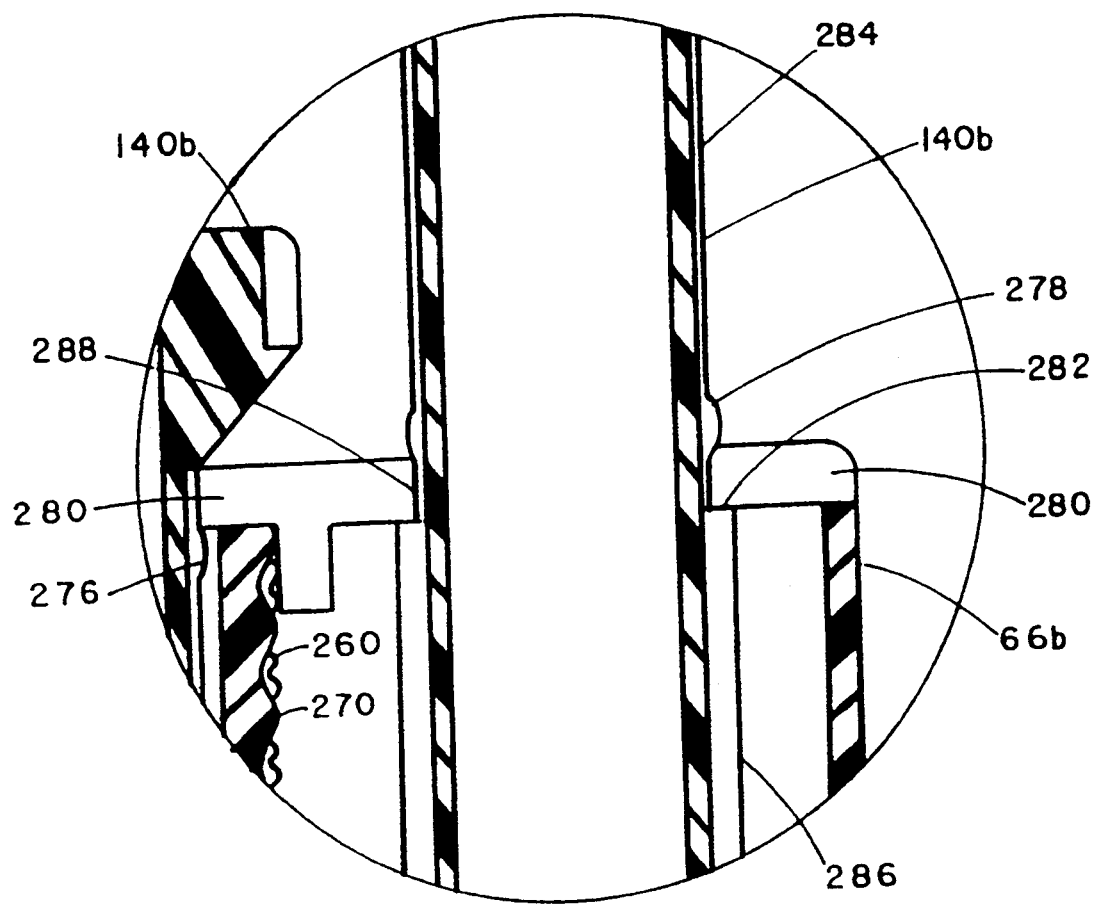
FIG. 13A is an enlarged view taken along line 13A—13A of FIG. 13.

As seen in FIGS. 13 and 13A, telescoping drive extensions 140b include a pair of axially spaced detent elements 276, 278. With drive extension 140b in the retracted position, detent element 276 engages below the upper edge 280 of sliding body 66b. When drive extension 140b is in the extended position, detent element 278 is positioned above upper edge 280. Further proximal axial movement of drive extension 140b is prevented by the engagement of ledge 282 abutting upper edge 280. Ledge 282 is created by virtue of the fact that the upper portion 284 of drive extension 140b is of a smaller diameter than the lower portion 286 so that lower portion 286 cannot pass through the openings 288 created in upper edge 280 of sliding body 66b.

To use variable proportion dispenser 2b, the user first determines the proportion of pharmaceuticals to be administered. Sliding body 66b, together with dose adjusters 60b, 61b, is moved in the distal direction as indicated by a large arrow in FIG. 14. Telescoping drive extension 140b of dose adjuster 61b is moved proximally as is illustrated in FIG. 12 to permit the user to rotate drive extension 140b without interference from the similar drive extension of dose adjuster 60b. As indicated in the Figures, the upper ends of drive extensions 140b can be shaped differently so that the user has a tactile indication of which pharmaceutical is being dosed. Drive extension 140b is then rotated, as indicated in FIG. 13, an appropriate number of turns. The number of turns is indicated tacitly and aurally through the engagement of detent springs 266 with grooves 264 formed in threaded portions 138b. While the preferred embodiment has two such grooves 264 formed in each threaded portion 138b, a greater or lesser number of grooves can be used as well. A particular dose is also indicated by the axial position of the corresponding dose indicator 150b as it moves beneath dose indicator viewing window 212.

Figure 14:
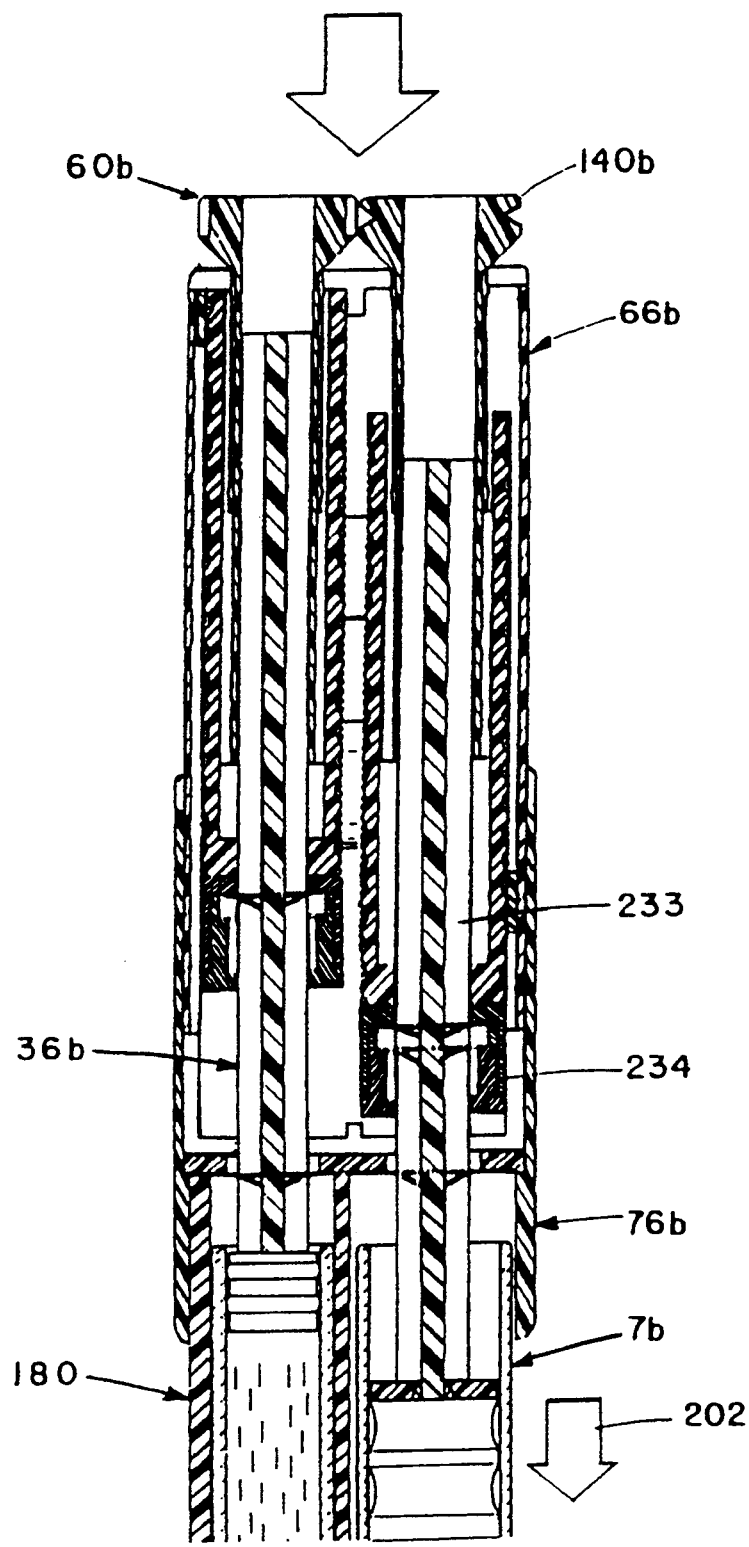
FIG. 14 shows the dispenser of FIG. 13 after the sliding body has been forced in the distal direction as shown by the arrows and after the right-hand drive extension has been telescoped back into the threaded portion of the dose adjuster.
Figure 15:
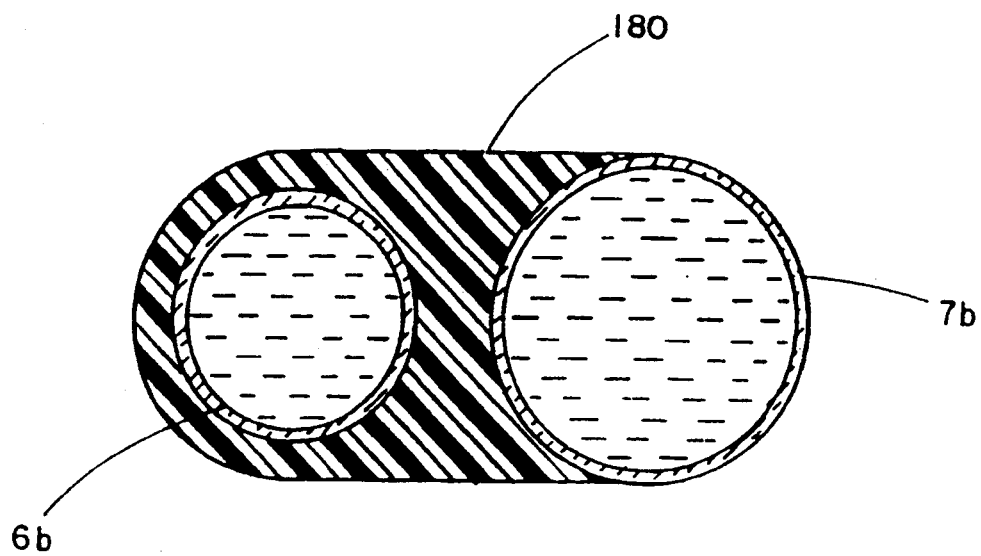
FIG. 15 is a cross-sectional view taken along line 15—15 of FIG. 11.

After the appropriate dose is achieved, drive extension 140b for dose indicators 51b is returned in the distal direction and the other drive extension is pulled in the proximal direction where the dosing steps are repeated. With telescoping drive extensions 140b in the retracted position of FIG. 14, a shipping cap 290 is removed from keeper 112 and a needle assembly 20 is mounted to keeper 112. By comparing FIGS. 13 and 14, it is seen that distal end 262 of threaded portion 138b of dose adjuster 61b contacts second proximal rachet assembly 234 and drives assembly 242 distally in the direction of arrow 202. Rachet disks 244 of rachet assembly 234 engage drive stem 37b thus driving the drive stem in the distal direction 202 causing the drive stem to force drive disk 204 against piston 46 to force piston to barrel 50b as shown in FIG. 14. In the example of FIGS. 13 and 14, dose adjuster 60b was set at zero so that no axial movement was imparted to drive stem 36b. If a mixture of the two pharmaceutical components were desired, dose adjuster 60b would have been adjusted to provide the desired amount of pharmaceutical from cartridge 6b, such pharmaceutical would have been dispensed during the delivery stroke suggested in FIGS. 13 and 14.

FIGS. 19-25 disclose a further embodiment of the invention in which a variable proportion dispenser 2c is shown together with a cartridge replacement assembly 302. Dispenser 2c is similar to dispenser 2b shown in FIGS. 9-18B, with like reference numerals referring to like elements. The main distinction between dispenser 2c and the other dispensers is the ability of the user to replace a spent pharmaceutical cartridge and reset the drive stem to its initial position after the cartridge has been replaced.

Figure 19:
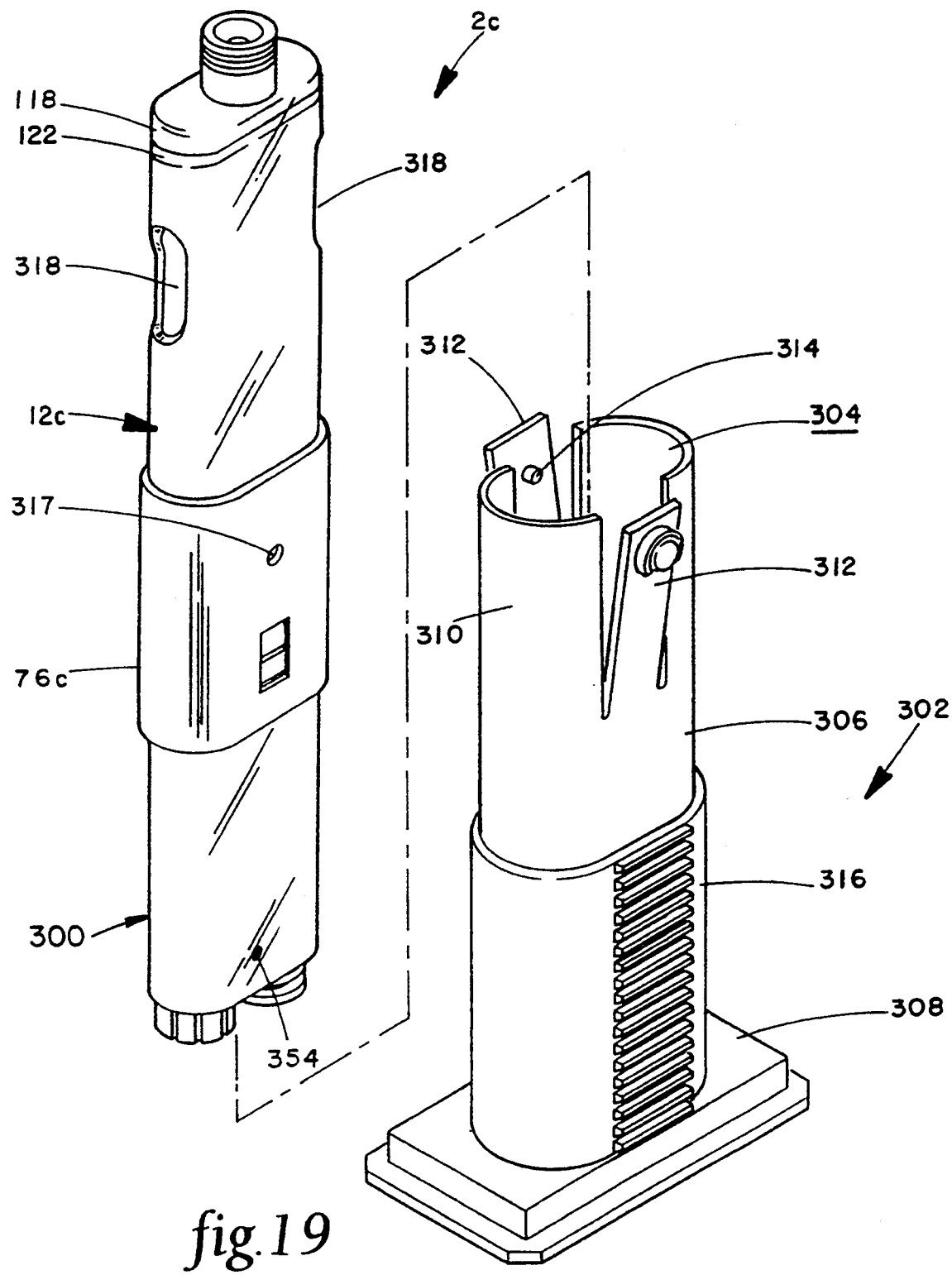
FIG. 19 is an isometric view of a further embodiment of a variable proportion dispenser shown together with a cartridge replacement assembly used to separate the dispenser housing and cartridges therewith from the remainder of the dispenser to permit removal and replacement of cartridges from the housing and resetting of the drive stems.
Figure 20:
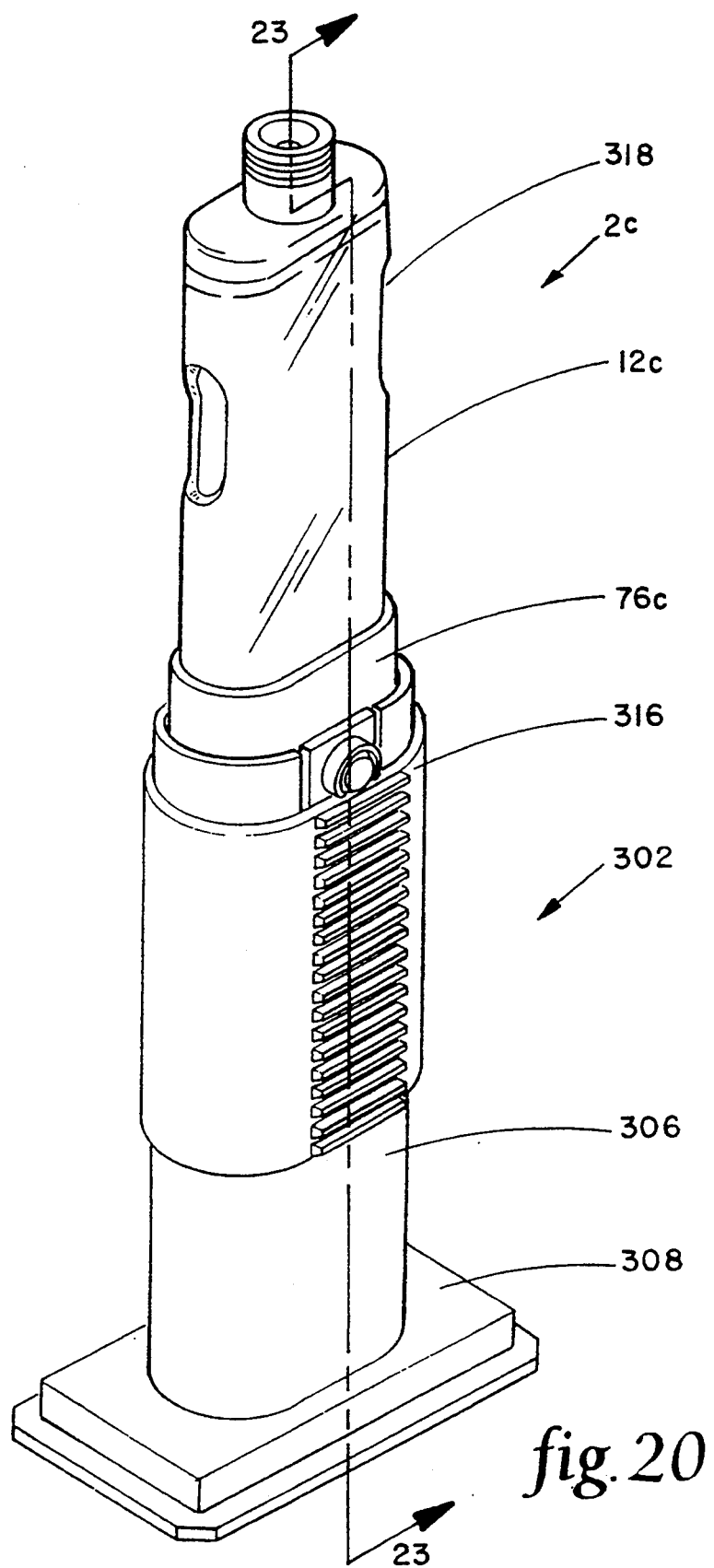
FIG. 20 illustrates the dispenser and assembly of FIG. 19 with the dispenser fully mounted within the assembly and the sleeve of the assembly slid upwardly.

Variable proportion dispenser 2c is shown in FIG. 19 prior to insertion of a clear plastic sliding body housing 300 (which houses sliding body 66e as discussed below) into the interior 304 of cartridge replacement assembly 302. Assembly 302 includes an elongate, oval body 306 supported vertically by a base 308. The upper end 310 of body 306 has a pair of normally outwardly extending arms 312 with a pair of disengagement pegs 314 extending inwardly from the distal ends thereof. Assembly 302 also includes a sleeve 316 which is movable from the lowered position of FIG. 19 to the raised position of FIG. 20. Doing so, with body housing 300 inserted therein as shown in FIG. 20, biases disengagement pegs 314 towards and into appropriately positioned holes 317 formed in limit guide 76c. This permits the release of housing 12c from limit guide 76c and thus from the remainder of assembly 302 suggested in FIG. 21 and as discussed in more detail below. Doing so permits the user to remove a spent cartridge 6b, again as suggested in FIG. 21. To aid removal, housing 12c has a pair of cutouts 318 which permit user access to the shoulders of cartridges 6b.

Figure 21:
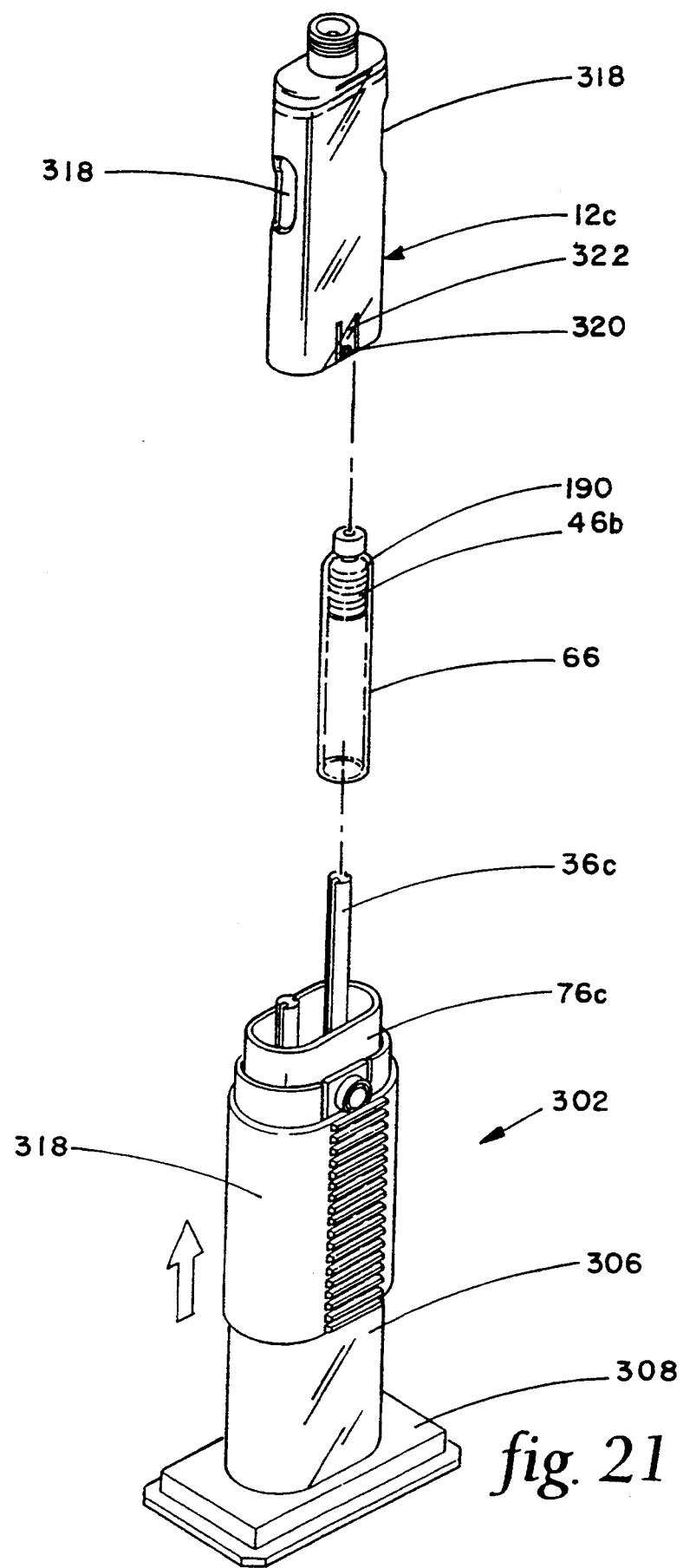
FIG. 21 is a partially exploded isometric view of the dispenser and assembly of FIG. 20 with the dispenser housing separated from the remainder of the dispenser, one of the pharmaceutical cartridges removed from the housing but prior to return of the associated drive stem to its initial position.

The cartridge removed from housing 12c in FIG. 21 as shown with piston 46b adjacent the septum end 190 of the cartridge. This position of the piston within the now-empty cartridge is suggested by the extended position of the associated drive stem 36c. As is discussed in more detail below, the user can now replace the spent or empty cartridge 6b with a filled cartridge, return drive stem 36c back to its original position and remount a pharmaceutical cartridge containing housing 12c back into limit guide 76c. The user can then slide sleeve 316 back down towards base 308 to the position of FIG. 19 to cause housing 12c to be resecured to sleeve 76c and allow removal of dispenser 2c for further use.

Figure 26A:
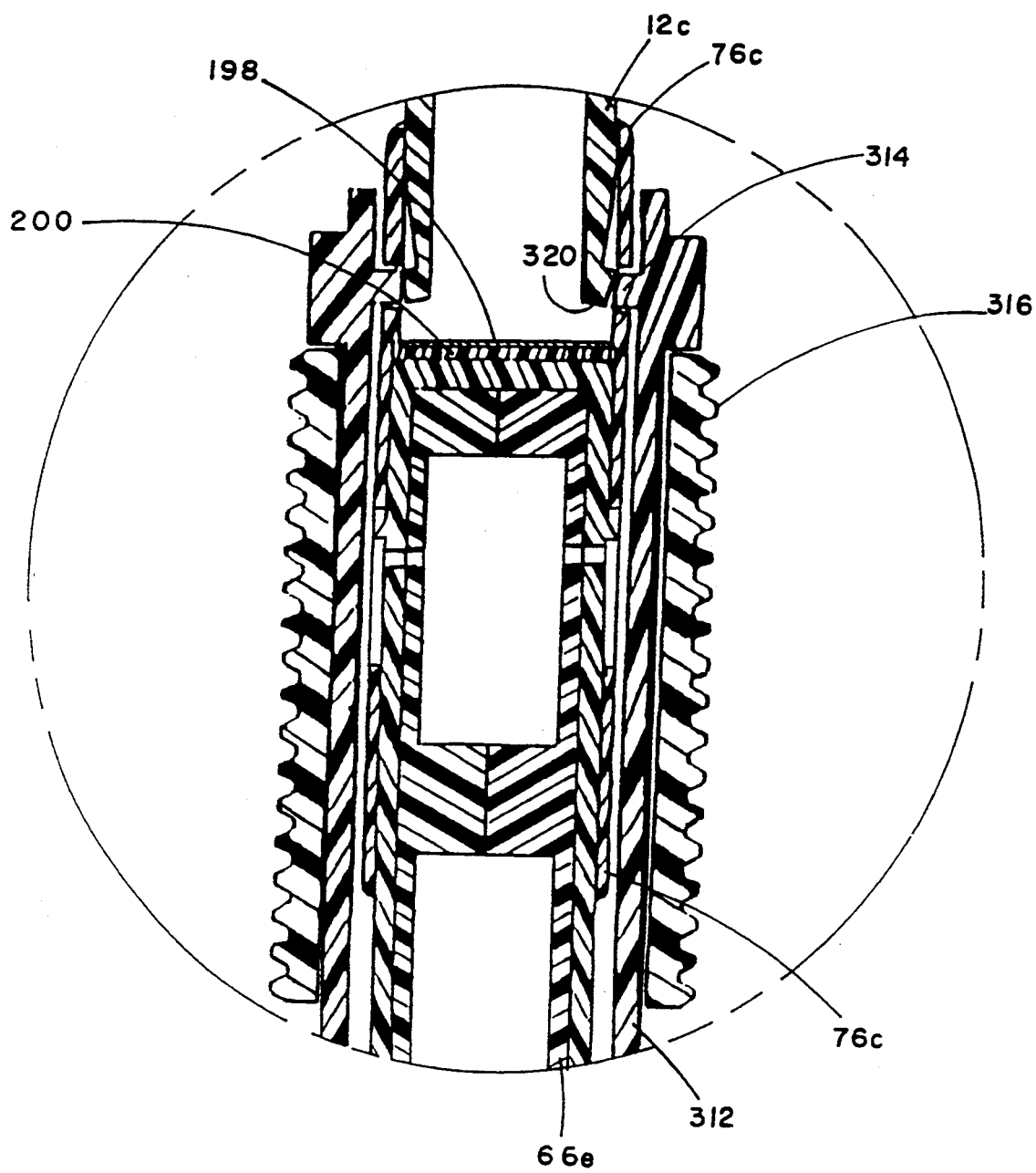
FIG. 26A is an enlarged view of a portion of FIG. 26 showing how the disengagement pegs of the body of the cartridge replacement assembly biases the engagement pegs of the dispenser housing inwardly to permit the dispenser housing to be separated from the remainder of the variable proportion dispenser as suggested in FIG. 24.

FIG. 22 illustrates the embodiment of FIGS. 19-21 in an exploded isometric view. Most of the elements are substantially the same as or identical to the variable proportion dispenser 2b and thus will not be described again. In the prior embodiments guide 76b is affixed to housing 12b in a permanent manner, such as using an adhesive. However, with this embodiment, limit guide 76c is releasably secured to housing 12c by the engagement of a pair of engagement pegs 320 which extend outwardly from outwardly biased arms 322 at the distal end 324 of housing 12c. See FIGS. 25, 26, 26A. When limit guide 76c is mounted over distal end 324 of housing 12c, arms 322 are biased inwardly to permit engagement pegs 320 to clear. Engagement pegs 320 then become aligned with and inserted into holes 317 on either side of limit guide 76c to secure limit guide 76c to housing 12c. While limit guide 76c could be removed from housing 12c using appropriate tools inserted into holes 317, this is preferably accomplished using cartridge replacement assembly 302 as described below.

Dispenser 2c includes two sets of ratchet assemblies which act as one way drivers 326. One-way drivers are made up of distal ratchet plate 198, retainer plate 200, ratchet disks 244 and a pair of spacers 328. One-way drivers 326 operate in the same manner as in the embodiment of FIG. 10. However, positioned between ratchet disks 244 and retainer plate 200 are a pair of ratchet release collars 330, shown in more detail in FIG. 22B. Ratchet release collars 330 are used to dilate fingers 250 extending inwardly from distal ratchet plate 198 when it is desired to release drive stems 36c. See FIGS. 23, 23A. Collars 330 include prongs 332 which engage fingers 250 when driven axially as discussed below. As can be seen from FIG. 22B, the interior 334 of collar 330 is generally H-shaped so that guide stem 36c can pass through the collar. Collar 330 is free to slide along drive stem 36c and thus normally does not interfere with the action of ratchet plate 198.

Figure 22A:
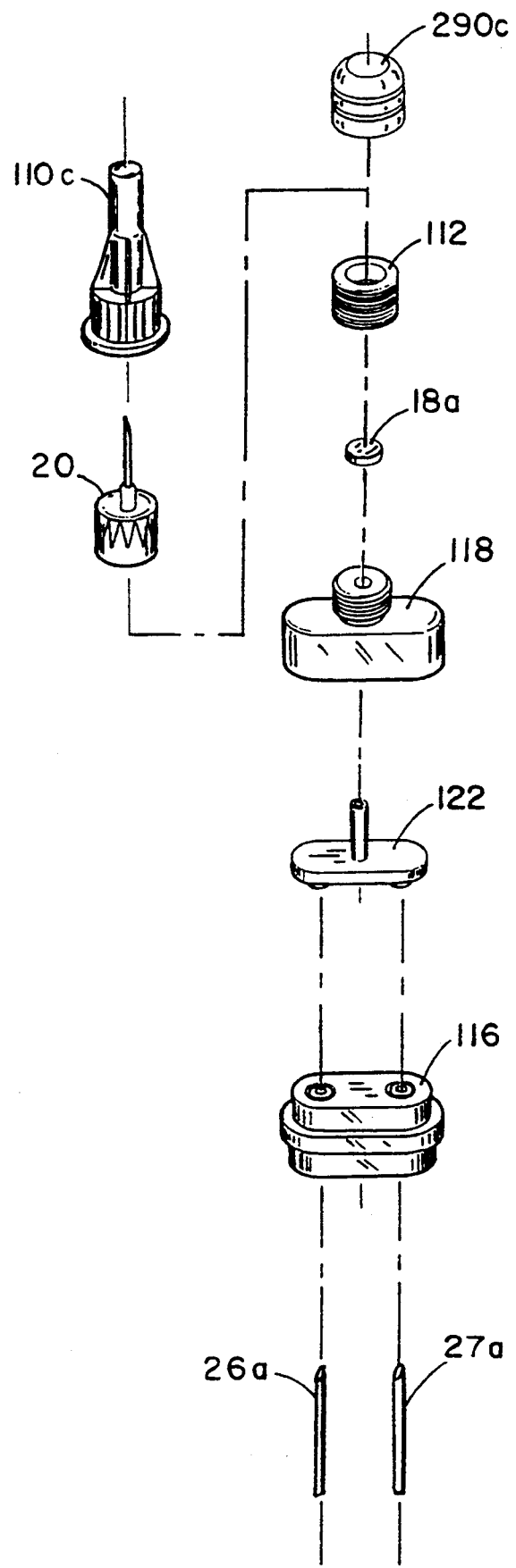
FIGS. 22A and 22B are enlarged isometric views of the ratchet release fork and ratchet release collar of FIG. 22.
Figure 22C:
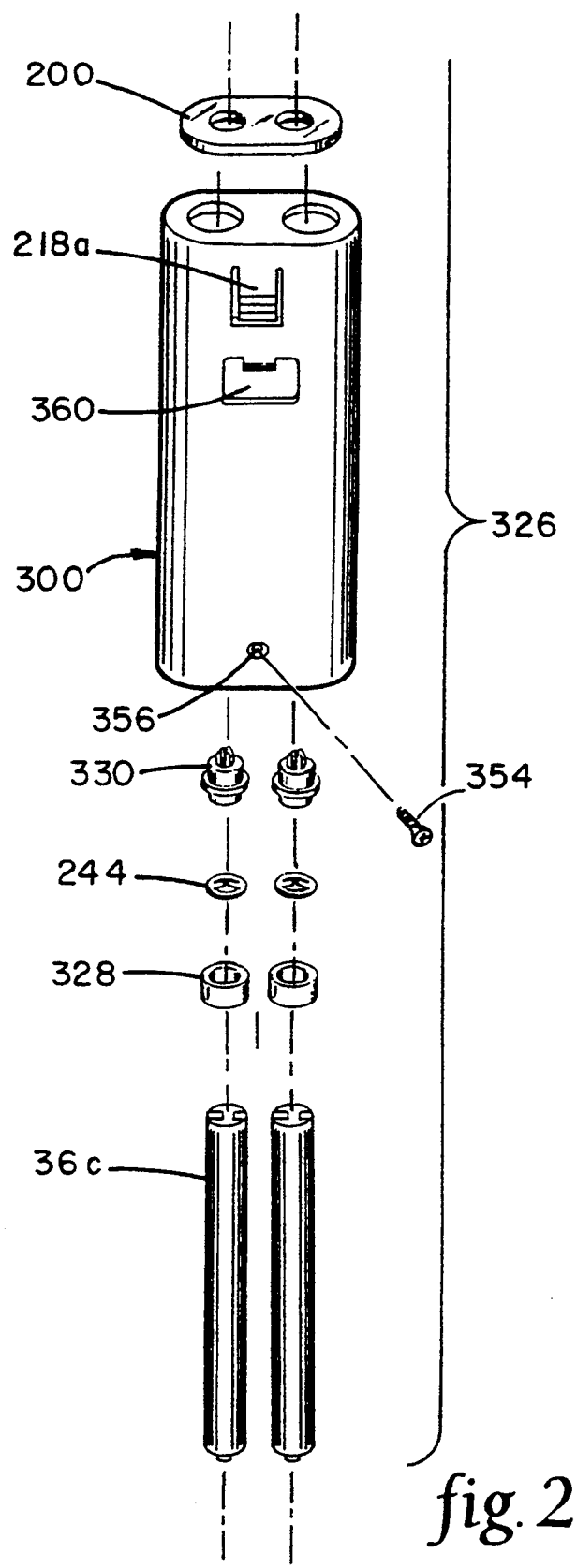
FIG. 22 is an exploded isometric view of the dispenser and assembly of FIG. 20.
Figure 22D:
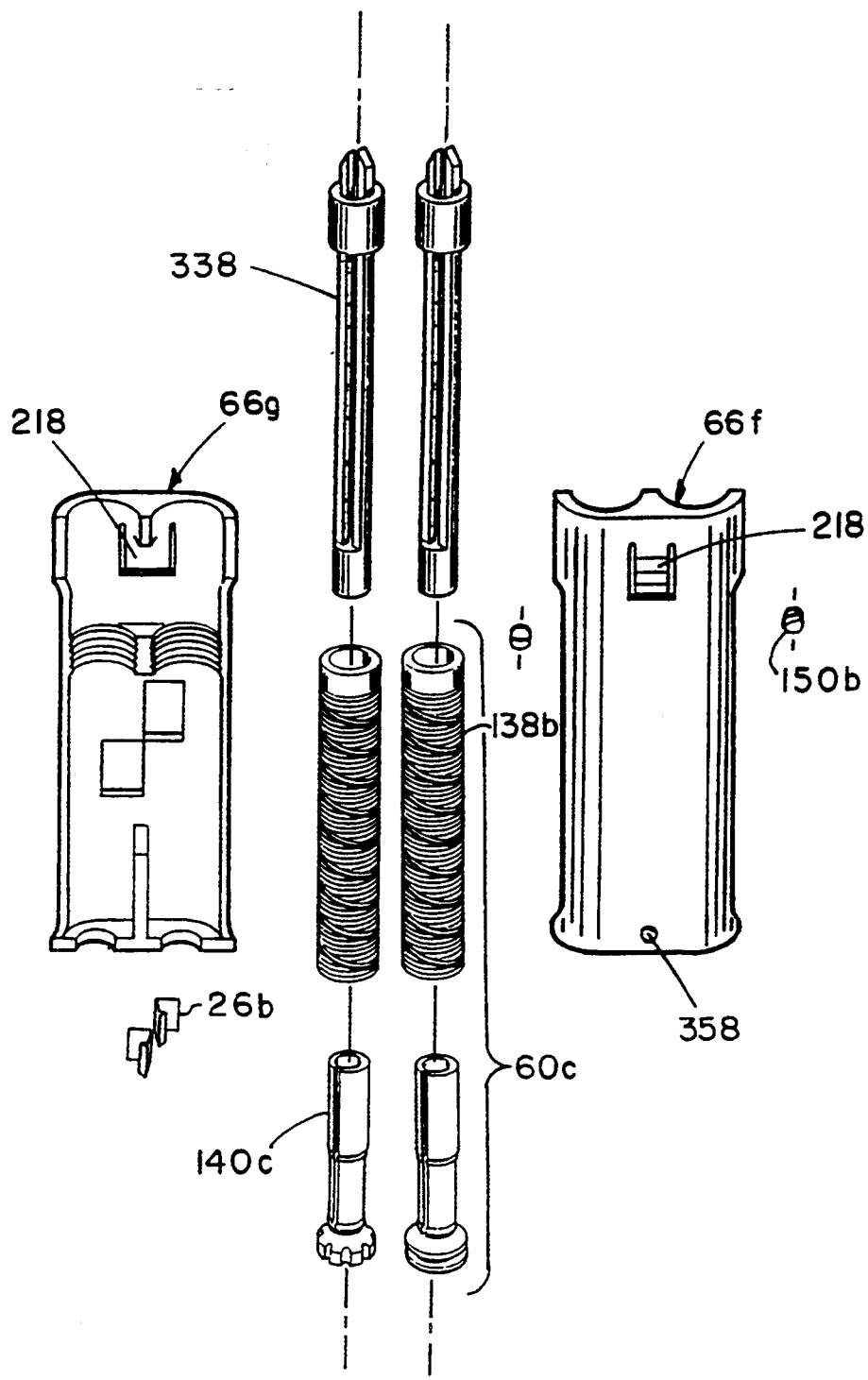
Figure 22E:
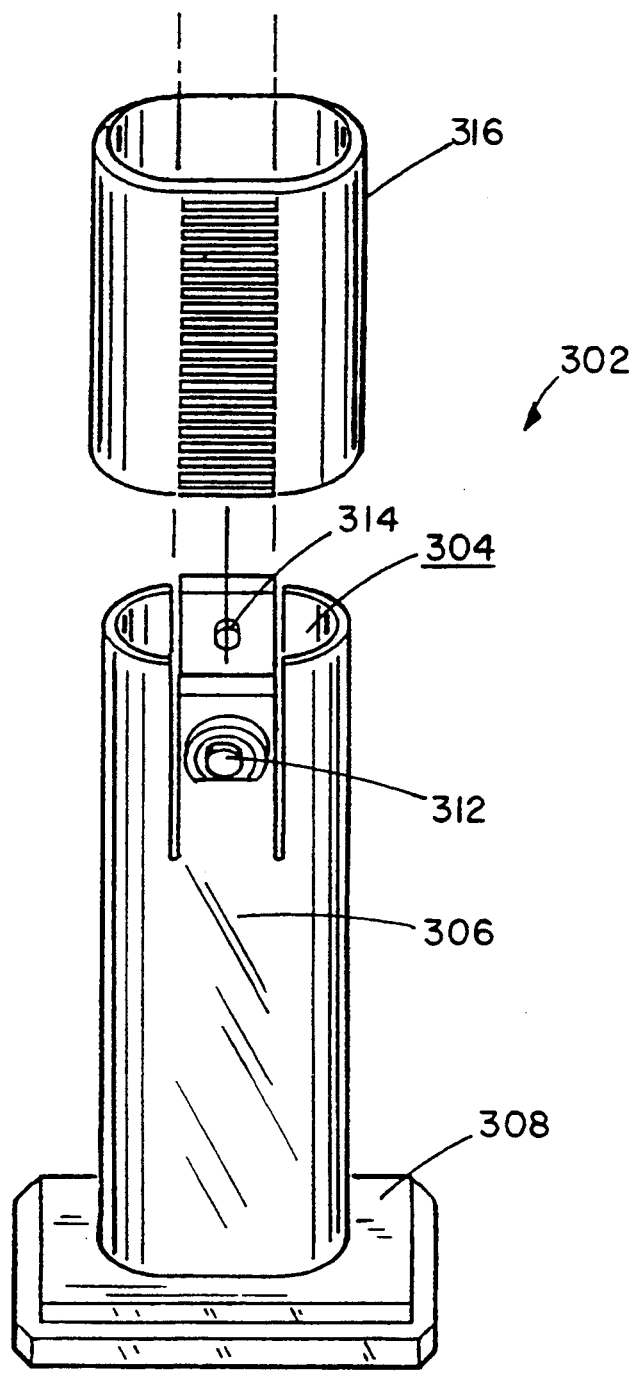
Figure 22F:
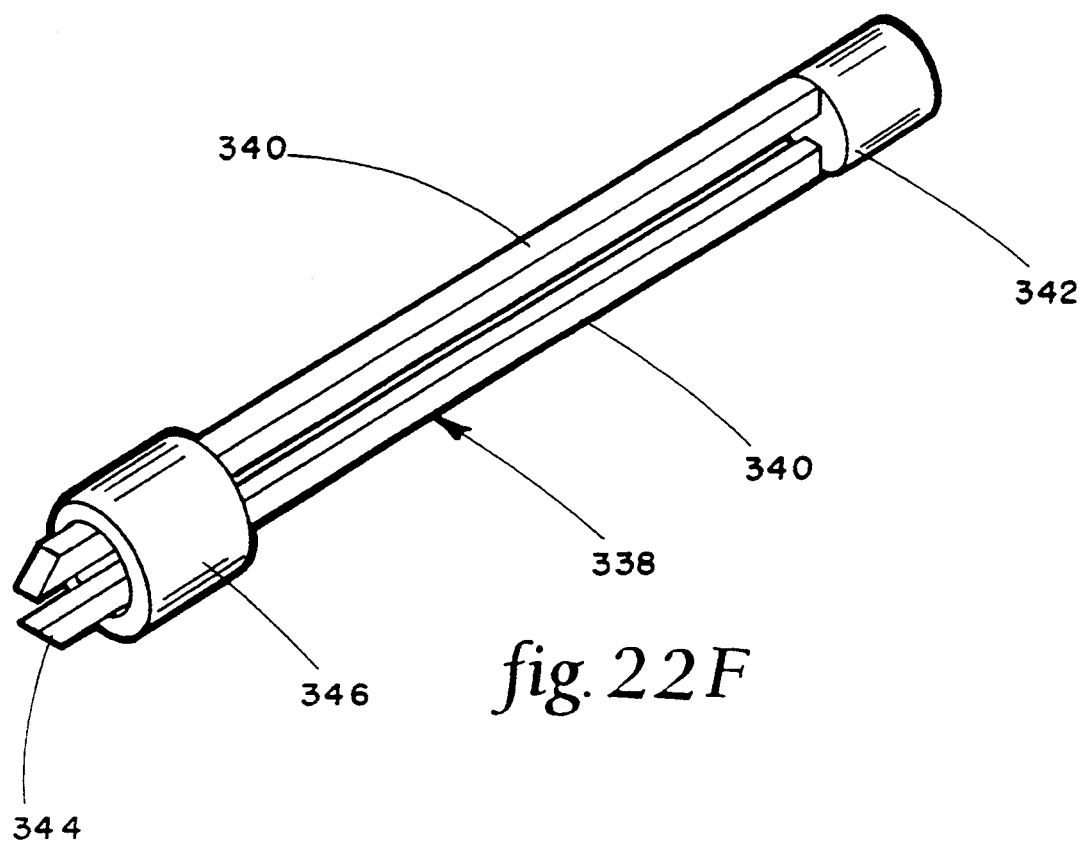
Figure 22G:
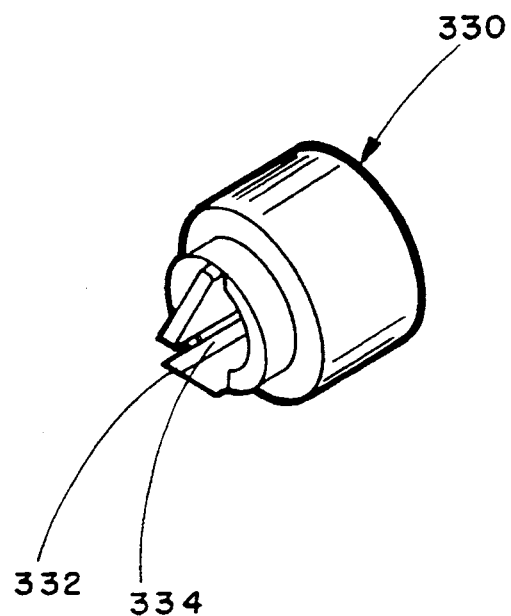

Dispenser 2c also includes a pair of ratchet release forks 338 shown in FIG. 22A. Ratchet release fork 338 is similar to ratchet release collar 330 and includes a pair of prongs 340 extending from a plug 342 at a proximal end to a pair of prong ends 344 at a distal end thereof. A collar 346 is secured adjacent prong ends 344 to both stabilize prongs 340 and press against spacers 328, see FIG. 23A, when it is desired to release drive stems 36c. Forks 338 are mounted within hollow telescoping drive extensions 140c. Plugs 342 of release forks 348 are thus accessible through openings 348 (see FIG. 23) at the proximal ends of drive extensions 140c.

A final difference between assembly 2b and assembly 2c relates to the use of clear sliding body housing 300. Sliding body 66e (made up of body halves 66f and 66g) is mounted through the open proximal end 350. Sliding body 66e is sized to fit somewhat snugly within housing 300 and is secured therein by a screw 354 which passes through a through-hole 356 in housing 300 and into a threaded hole 358 in sliding body half 66f. Housing 300 includes a pair of spring tabs 218a which engage openings 220 in limit guide 76c. Spring tabs 218 are positioned to lie adjacent spring tabs 218a and will move inwardly when necessary to permit the necessary inward deflection of spring tabs 218a.

Sliding body housing 300 also includes a recess 360, preferably colored green. This green recess 360 indicates when dispenser 2c is ready for an injection. That is, moving sliding body 300 in a proximal direction, that is downwardly in FIG. 19, away from limit guide 76c will expose at least a part of green recess 360. After the injection green recess 360 is once again covered by limit guide 76c as shown in FIG. 19.

Figure 23:
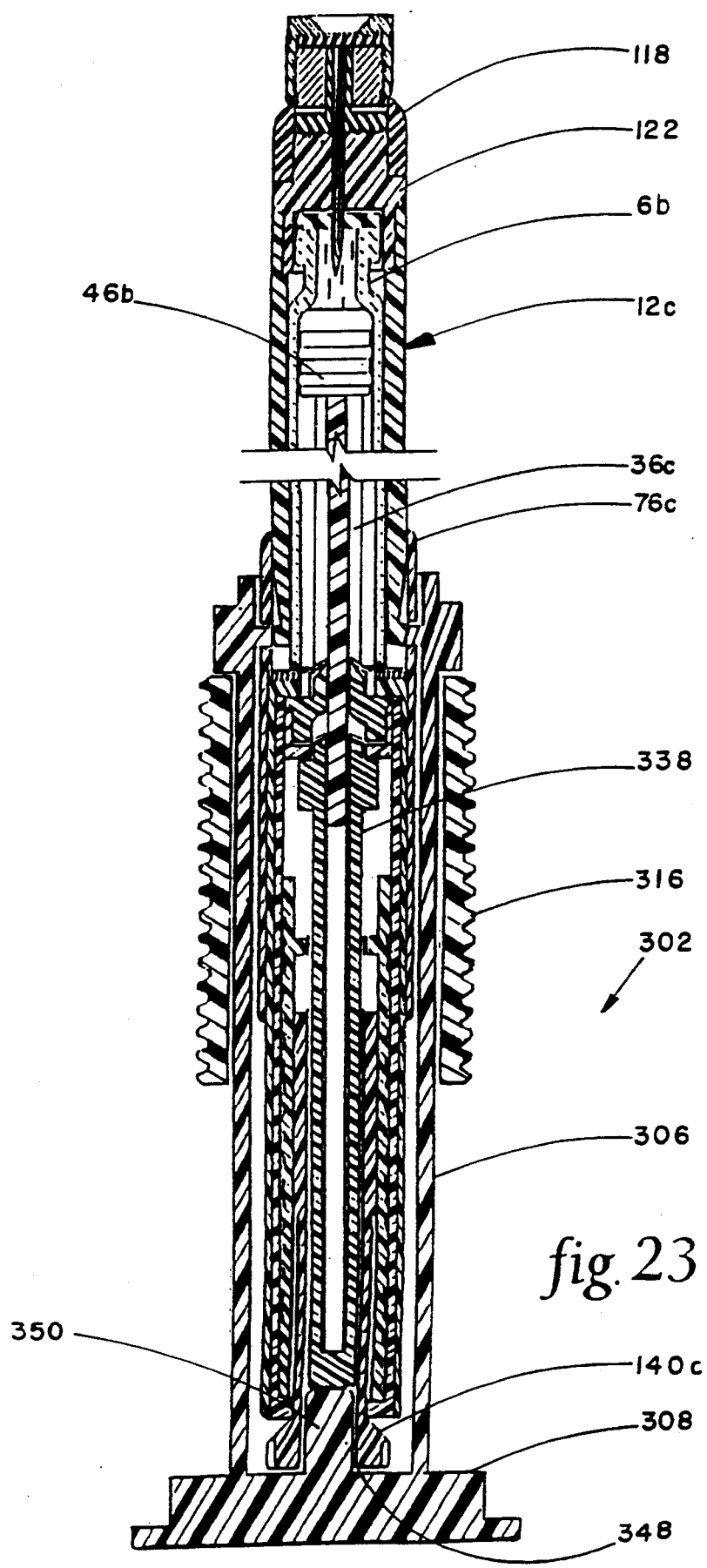
FIG. 23 is a cross-sectional view taken along line 23—23 of FIG. 20 passing through a spent or exhausted pharmaceutical cartridge.
Figure 23A:
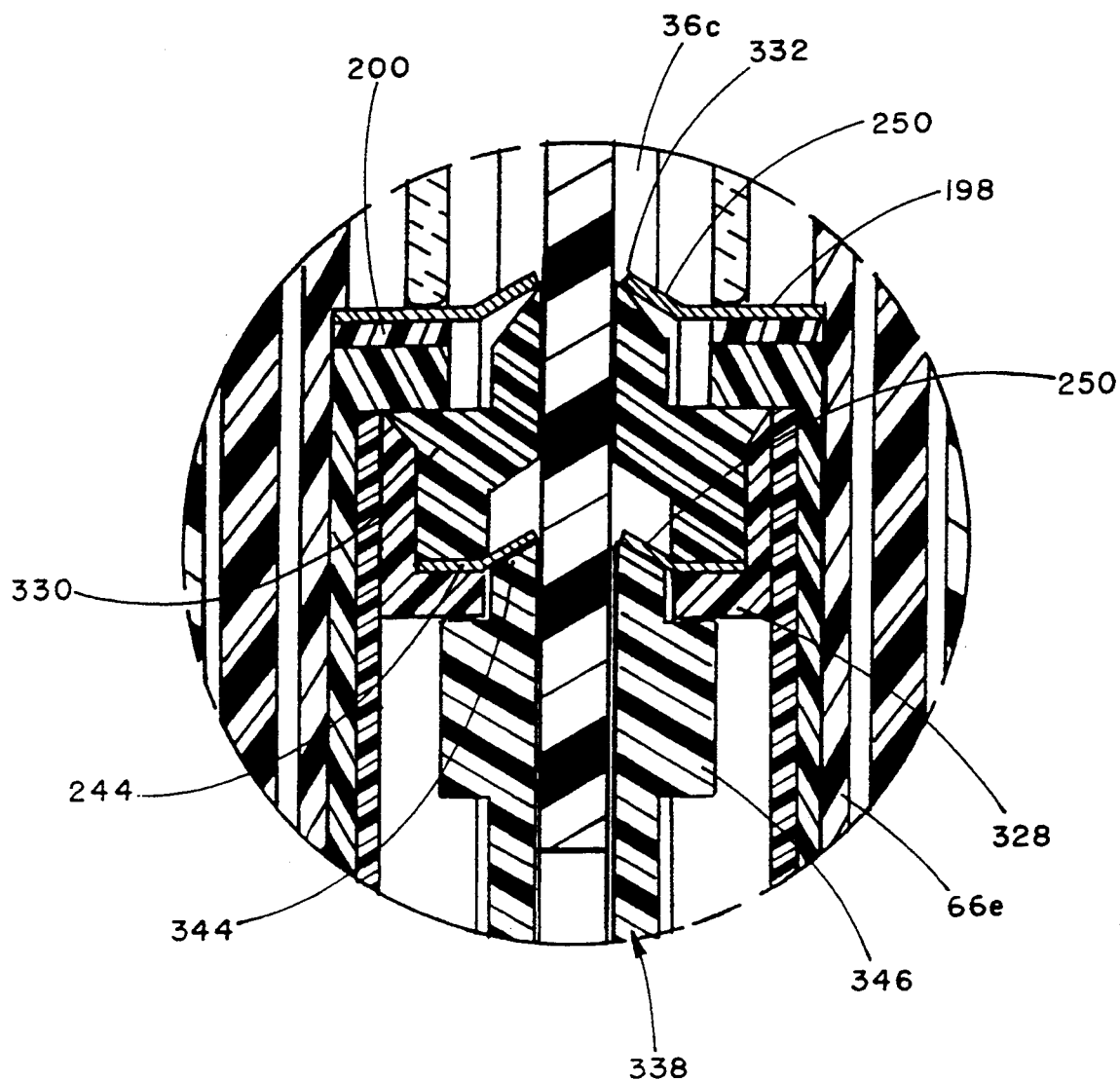
FIG. 23A is an enlarged view of a central portion of FIG. 23 illustrating the disengagement of the fingers of the ratchet elements from the drive stems.
Figure 24:
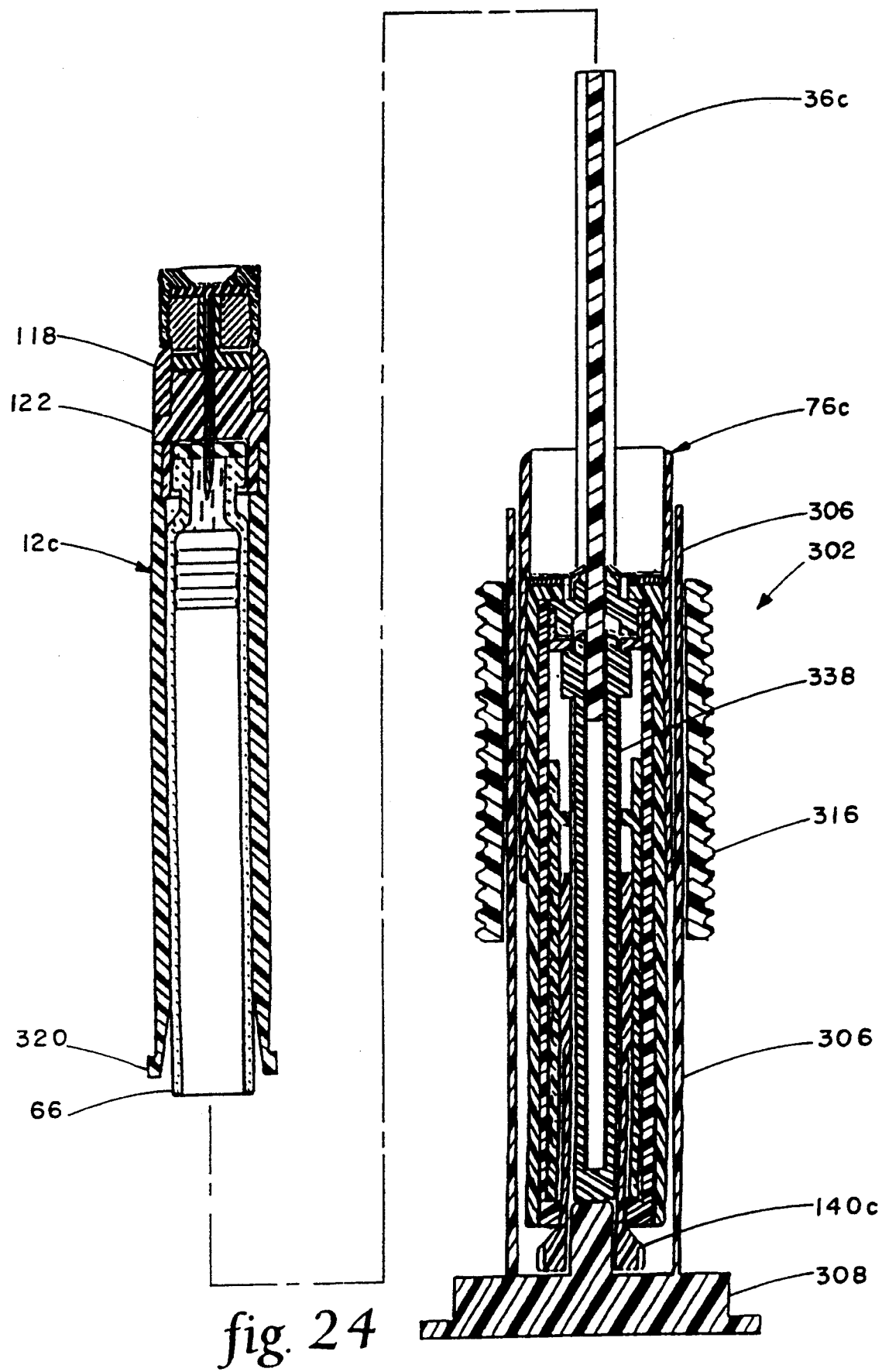
FIG. 24 shows the dispenser and assembly of FIG. 23 with the dispenser housing and cartridges therewith removed from the remainder of the dispenser.
Figures 25, 26:
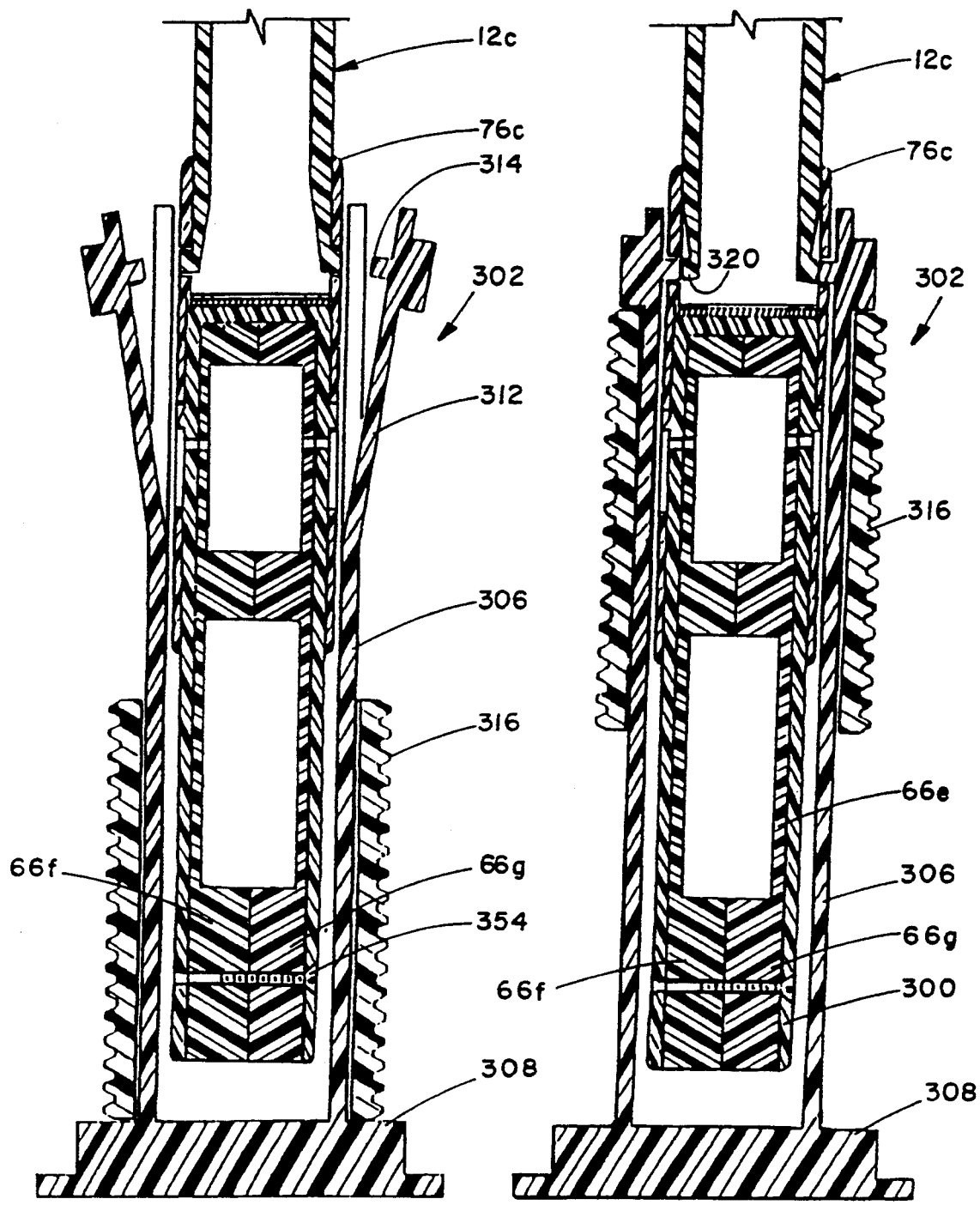
FIG. 25 is a partial cross-sectional view of the dispenser and cartridge replacement assembly of FIG. 20 taken through the center prior to sliding the sleeve upwardly.
FIG. 26 shows the apparatus of FIG. 25 after the sleeve has been raised to the position of FIG. 20.

For the following discussion of the use of dispenser 2c and cartridge replacement assembly 302, we will assume that the cartridge 6c on the right hand side of dispenser 2c is essentially empty, that is, spent or used. To replace cartridge 6c, the user inserts the proximal end of dispenser 2c, that is sliding body housing 300, into interior 304 of body 306 of assembly 302 as suggested in FIGS. 19 and 25. The user then slides sleeve 316 upwardly to the position of FIGS. 20 and 26. This causes disengagement pegs 314 to press on engagement pegs 320, see FIG. 26A, and thus forces pegs 314 out of holes 317. Doing so permits the user to separate dispenser housing 12c, carrying cartridges 6b therewith, from the remainder of dispenser 2c as shown in FIG. 24. The user then inserts his or her finger through cutout 318, which provides access to the shoulder at septum end 190 of cartridge 6b, to push the cartridge out of housing 12c as shown in FIG. 21. At this point pegs 350 extend upwardly from base 308 and press against plugs 342 of latch release forks 338 forcing prong ends 344 against fingers 250 of ratchet disks 244 and forcing fingers 250 away from drive stems 36c as shown in FIG. 23A. Doing so also drives prongs 332 of ratchet release collar 330 against the fingers 250 of distal ratchet plate 198. The extended drive stem 36c, shown on the right size of FIG. 21, can then be pushed back down to the original or start position as suggested by the left-hand drive stem 36c of FIG. 21. A replacement cartridge 6b is then mounted into housing 12c and the combination inserted back into interior 304 of body 306. When fully seated therein, sleeve 316 is moved downwardly to the position of FIG. 25 which permits engagement pegs 320 to re-engage holes 317. The user can then remove the recharged dispenser 2c from cartridge replacement assembly 302 as suggested in FIG. 19.

Further modifications and variations can be made to the disclosed embodiments without departing from the subject of the invention as defined in the following claims. For example, the invention can be used with more than two containers.

What is claimed is:

1. A variable proportion dispenser comprising:

a housing;

first and second variable volume containers mounted to the housing and including first and second exits and first and second movable elements by which the contents of the first and second containers can be forced through said first and second exits as the first and second movable elements are moved from first and second starting positions towards first and second ending positions;

first and second drive stems drivingly coupled to the first and second movable elements, the first and second drive stems including axially extending drive surfaces;

a reciprocal drive assembly configured to drive the first and second movable elements from the first and second starting positions towards the first and second ending positions, the reciprocal drive assembly including:

first and second reciprocating drivers, including one-way drive elements, said one-way drive elements being configured to drivingly engage the first and second drive stems when the first and second reciprocating drivers are moved toward the first and second ending positions, the one-way drive elements configured to be drivingly disengaged from the first and second drive stems so that the first and second drive stems do not move when the first and second reciprocating drivers are moved away from the first and second ending positions;

first and second stroke adjusters for adjusting the relative distances the first and second reciprocating drivers and the first and second drive stems associated therewith travel during each cycle of the reciprocal driver so that the amounts and proportions of the contents of the first and second containers forced through the first and second exits during each of one or more cycles of the reciprocal drive assembly can be selected by the user while said amounts and proportions remain the same unless said relative distances are changed; and said drive surfaces and said reciprocating drivers adapted to permit a range of said relative distances to be chosen by the user through adjustment of said stroke adjusters; and means for selectively releasing the one-way drive elements from the first and second drive stems.

2. A variable proportion dispenser comprising:

a housing;

first and second variable volume containers mounted to the housing and including first and second exits and first and second movable elements by which the contents of the first and second containers Can be forced through said first and second exits as the first and second movable elements are moved from first and second starting positions towards first and second ending positions;

first and second drive stems drivingly coupled to the first and second movable elements, the first and second drive stems including axially extending drive surfaces;

a reciprocal drive assembly for reciprocally driving the first and second drive stems so to drive the first and second movable elements from the first and second starting positions towards the first and second ending positions in a cyclic manner, the reciprocal drive assembly including:

first and second reciprocating drivers, including one-way drive elements, drivingly coupled to the first and second drive stems along the drive surfaces by the one-way drive elements;

first and second stroke adjusters for adjusting the relative distances the first and second reciprocating drivers and the first and second drive stems associated therewith travel during each cycle of the reciprocal driver so that amounts and proportions of the contents of the first and second containers forced through the first and second exits during each of one or more cycles of the reciprocal drive assembly can be selected by the user while said amounts and proportions remain the same unless said relative distances are changed; and said drive surfaces and said reciprocating drivers adapted to permit a range of said relative distances to be chosen by the user through adjustment of said stroke adjusters;

means for selectively releasing the one-way drive elements from the first and second drive stems; and means for selectively separating at lest a portion of the housing and the variable volume containers therewith from the remainder of the dispenser to provide user access to the variable volume containers.

3. The dispenser of claim 2 further comprising container release means for holding the dispenser and for actuating the selectively separating means.

4. The dispenser of claim 3 wherein the container release means include a hollow support base, having a length, and a sleeve movable along the length of the support base.

5. The dispenser of claim 1 wherein the drive surfaces are smooth drive surfaces.

6. The dispenser of claim 1 wherein the variable volume containers include cartridges configured to contain pharmaceutical.

7. A variable proportion dispenser comprising:

a housing;

first and second variable volume containers mounted to the housing and including first and second exits and first and second movable elements by which the contents of the first and second containers can be forced through said first and second exits as the first and second movable elements are moved from first and second starting positions towards first and second ending positions;

first and second drive stems drivingly coupled to the first and second movable elements, the first and second drive stems including axially extending drive surfaces, the drive surfaces of the drive stems being at least partially defined by axially extending slots formed in the drive stems;

a reciprocal drive assembly for reciprocally driving the first and second drive stems so as to drive the first and second movable elements from the first and second starting positions towards the first and second ending positions in a cyclic manner, the reciprocal drive assembly including:

first and second reciprocating drivers, including one-way drive elements, drivingly coupled to the first and second drive stems along the drive surfaces by the one-way drive elements;

first and second stroke adjusters for adjusting the relative distances the first and second reciprocating drivers and the first and second drive stems associated therewith travel during each cycle of the reciprocal driver so the amounts and proportions of the contents of the first and second containers forced through the first and second exits during each of one or more cycles of the reciprocal drive assembly can be selected by the user while said amounts and proportions remain the same unless said relative distances are changed; and said drive surface and said reciprocating drivers adapted to permit a range of said relative distances to be chosen by the user through adjustment of said stroke adjusters; and means for selectively releasing the one-way drive elements from the first and second drive stems.

8. A variable proportion dispenser comprising:

a housing;

first and second variable volume containers mounted to the housing and including first and second exits and first and second movable elements by which the contents of the first and second containers can be forced through said first and second exits as the first and second movable elements are moved from first and second starting positions towards first and second ending positions;

first and second drive stems drivingly coupled to the first and second movable elements, the first and second drive stems including axially extending drive surfaces;

a reciprocal drive assembly for reciprocally driving the first and second drive stems so to drive the first and second movable elements from the first and second starting positions towards the first and second ending positions in a cyclic manner, the reciprocal drive assembly including:

first and second reciprocating drivers, including one-way drive elements, drivingly coupled to the first and second drive stems along the drive surfaces by the one-way drive elements, the one-way drive elements including spring arms positioned at an acute angle to the drive surfaces, the spring arms engaging the drive surfaces;

first and second stroke adjusters for adjusting the relative distances the first and second reciprocating drivers and the first and second drive stems associated therewith travel during each cycle of the reciprocal driver so the amounts and proportions of the contents of the first and second containers forced through the first and second exits during each of one or more cycles of the reciprocal drive assembly can be selected by the user while said amounts and proportions remain the same unless said relative distances are changed; and said drive surfaces and said reciprocating drivers adapted to permit a range of said relative distances to be chosen by the user through adjustment of said stroke adjusters; and means for selectively releasing the one-way drive elements from the first and second drive stems.

9. The dispenser of claim 8 wherein the selectively releasing means includes a releasing fork mounted coaxially within the reciprocating drivers and adapted to selectively engage the spring arms so to deflect said spring arms away from the drive surfaces.

10. The dispenser of claim 1 wherein the first and second stroke adjusters each include means for individually adjusting the amount each of said first and second drive stems moves during each cycle of the reciprocal drive assembly, each individual adjusting means including a rotatable dose control element by which a user selects said amounts and proportions of the contents of the respective first and second containers forced through the first and second exits.

11. The dispenser of claim 10 wherein each rotatable dose control element is an axially telescoping element to permit the user to easily rotatably manipulate one said dose control element without substantial interference from another said dose control element.

12. The dispenser of claim 1 wherein the reciprocal drive assembly includes means for independently adjusting the proportions of the contents of the first and second containers forced through the first and second exits during each cycle of the reciprocal drive assembly.

13. The dispenser of claim 1 further comprising means for indicating the amounts of the contents of each of the first and second containers which are to be forced through the first and second exits during each of the one or more cycles of the reciprocating drive means.

14. The dispenser of claim 13 wherein the indicating means includes first and second visual displays.

15. A variable proportion dispenser comprising:
a housing;
first and second variable volume containers mounted to the housing and including first and second exits and first and second movable elements by which the contents of the first and second containers can be forced through said first and second exits as the first and second movable elements are moved from first and second starting positions towards first and second ending positions;
first and second drive stems drivingly coupled to the first and second movable elements., the first and second drive stems including axially extending drive surfaces;
a reciprocal drive assembly for reciprocally driving the first and second drive stems so to drive the first and second movable elements from the first and second starting positions towards the first and second ending positions in a cyclic manner, the reciprocal drive assembly including:
first and second reciprocating drivers, including one-way drive elements, drivingly coupled to the first and second drive stems along the drive surfaces by the one-way drive elements;
first and second stroke adjusters for adjusting the relative distances the first and second reciprocating drivers and the first and second drive stems associated therewith travel during each cycle of the reciprocal driver so the amounts and proportions of the contents of the first and second containers forced through the first and second exits during each of one or more cycles of the reciprocal drive assembly can be selected by the user while said amounts and proportions remain the same unless said relative distances are changed; and
said drive surfaces and said reciprocating drivers adapted to permit a range of said relative distances to be chosen by the user through adjustment of said stroke adjusters;
means for selectively releasing the one-way drive elements from the first and second drive stems;
means for indicating the amounts of the contents of each of the first and second containers which are to be forced through the first and second exits during each of the one or more cycles of the reciprocating drive means, the indicating means includes first and second visual displays;
the housing having first and second sides facing in opposite directions, said first and second displays located at the first and second sides, respectively.

16. A variable proportions dispenser comprising:
a housing;
first and second variable volume containers mounted to the housing and including first and second exits and first and second movable elements by which the contents of the first and second containers can be forced through said first and second exits as the first and second movable elements are moved from first and second starting positions towards first and second ending positions;
first and second drive stems drivingly coupled to the first and second movable elements, the first and second drive stems including axially extending drive surfaces;
a reciprocal drive assembly for reciprocally driving the first and second drive stems so to drive the first and second movable elements from the first and second starting positions towards the first and second ending positions in a cyclic manner, the reciprocal drive assembly including:
first and second reciprocating drivers, including one-way drive elements, drivingly coupled to the first and second drive stems along the drive surfaces by the one-way drive elements;
first and second stroke adjustors for adjusting the relative distances the first and second reciprocating drivers and the first and second drive stems associated therewith travel during each cycle of the reciprocal driver so the amounts and proportions of the contents of the first and second containers forced through the first and second exits during each of one or more cycles of the reciprocal drive assembly can be selected by the user while said amounts and proportions remain the same unless said relative distances are changed; and
said drive surfaces and said reciprocating drivers adapted to permit a range of said relative distances to be chosen by the user through adjustment of said stroke adjusters;
means for selectively releasing the one-way drive elements from the first and second drive stems; and
means for indicating the amounts of the contents of each of the first and second containers which are to be forced through the first and second exits during each of the one or more cycles of the reciprocating drive means, the indicating means including:
first and second indicators coupled to and axially movable with the first and second movable elements; and
means for magnifying the axial movement of the first and second indicators over the corresponding axial movement of the first and second movable elements.

17. The dispenser of claim 1 wherein the reciprocal drive assembly includes a sliding body slidably mounted to the housing.

18. The dispenser of claim 17 further comprising a first indicator movably mounted to the sliding body and coupled to the first stroke adjuster to indicate the amount of the contents of the first variable volume container which is forced through the first exit during each of the one or more cycles of the reciprocal drive assembly.

19. The dispenser of claim 18 wherein the first stroke adjuster is threadably mounted to the sliding body for movement therewith.

20. The dispenser of claim 19 wherein the first stroke adjuster includes a first set of external threads, having a first direction of twist, formed thereon by which the first stroke adjuster is threadably mounted to the slidable body.

21. A variable proportion dispenser comprising:
a housing;
first and second variable volume containers mounted to the housing and including first and second exits and first and second movable elements by which the contents of the first and second containers can be forced through said first and second exits as the first and second movable elements are moved from first and second starting positions towards first and second ending positions;

first and second drive stems drivingly coupled to the first and second movable elements, the first and second drive steps including axially extending drive surfaces;

a reciprocal drive assembly for reciprocally driving the first and second drive stems so to drive the first and second movable elements from the first and second starting positions towards the first and second ending positions in a cyclic manner, the reciprocal drive assembly including:

first and second reciprocating drivers, including one-way drive elements, drivingly coupled to the first and second drive stems along the drive surfaces by the one-way drive elements;

first and second stroke adjusters for adjusting the relative distances the first and second reciprocating drivers and the first and second drive means associated therewith travel during each cycle of the reciprocal driver so the amounts and proportions of the contents of the first and second containers forced through the first and second exits during each of one or more cycles of the reciprocal drive assembly can be selected by the user while said amounts and proportions remain the same unless said relative distances are changed;

said drive surfaces and said reciprocating drivers adapted to permit a range of said relative distances to be chosen by the user through adjustment of said stroke adjusters; and a sliding body slidably mounted to the housing;

means for selectively releasing the one-way drive elements from the first and second drive stems; and a first indicator movably mounted to the sliding body and coupled to the first stroke adjuster to indicate the amount of the contents of the first variable volume container which is forced through the first exit during each of the one or more cycles of the reciprocal drive assembly, the first stroke adjuster being threadably mounted to the sliding body for movement therewith, the first stroke adjuster including a first set of external threads, having a first direction of twist, formed thereon by which the first stroke adjuster is threadably mounted to the slidable body, the first stroke adjuster including a second set of external threads, having a second direction of twist, formed at least partially coextensively with the first set of external threads, the first indicator engaging the second set of external threads.

22. The dispenser of claim 21 wherein the second set of external threads have a pitch which is one or more times the pitch of the first set of external threads.

23. A variable proportion dispenser comprising:

a housing;

first and second pharmaceutical-containing cartridges mounted within the housing, the cartridges each including a movable piston, an exit end and a pharmaceutical between the piston and the exit end;

a reciprocating drive assembly comprising:

first and second drive stems adapted to engage the pistons of the first and second cartridges to drive the contents of the cartridges through the exit ends;

a sliding body slidably mounted to the housing for movement in delivery and return directions;

first and second reciprocating drivers, carried by the sliding body, including one-way drive elements coupled to the first and second drive stems, the one-way drive elements and the first and second drive stems configured so that the first and second reciprocating drivers move the first and second drive stems only towards the first and second cartridges during the movement of the sliding body;

means for adjusting the distance the first and second reciprocating drivers move the first and second drive stems towards the first and second cartridges during the movement of the sliding body in the delivery direction; and the stroke adjusting means includes an axially extending first dose adjuster element having first and second sets of opposite-hand threads formed at least partially coextensively along an outer surface thereof, the first set of threads engaging the sliding body so that the first dose adjuster moves with the sliding body;

an indicator movably mounted to the sliding body for axial movement along the sliding body and for engaging the second set of threads, so that rotary adjustment of the first dose adjuster element causes the indicator to move relative to the sliding body by virtue of the movement of the first dose adjuster element within the sliding body and by virtue of the movement of the indicator along the second set of threads;

means for selectively releasing the one-way drive elements from the first and second drive stems; and means for selectively separating at least a portion of the housing and the variable volume containers therewith from the remainder of the dispenser to provide user access to the variable volume containers.

24. The dispenser of claim 23 further comprising container release means for holding the dispenser and for actuating the selectively separating means.

25. The dispenser of claim 24 wherein the container release means include a hollow support base, having a length, and a sleeve movable along the length of the support base.

26. The dispenser of claim 23 wherein the first and second drive stems have smooth drive surfaces and the one-way drive elements include portions which drivingly engage the drive surfaces to permit a continuous range of said distances to be chosen by the user.

27. The dispenser of claim 26 wherein the one-way drive elements include spring arms oriented at acute angles to the drive surfaces and having arm ends touching the drive surfaces.

* * * * *

UNITED STATES PATENT AND TRADEMARK OFFICE
CERTIFICATE OF CORRECTION

PATENT NO. : 5,423,752
DATED : June 13, 1995
INVENTOR(S) : Terry M. Haber, et al It is certified that error appears in the above-indentified patent and that said Letters Patent is hereby corrected as shown below:

On the title page: [*] Notice" should read [*] Notice: The term of of this patent shall not extend beyond the expiration date of Pat. No: 5,271,527.

Signed and Sealed this

Twenty-first Day of November, 1995

*Attest:*

BRUCE LEHMAN

*Attesting Officer*  *Commissioner of Patents and Trademarks*